US010418126B2

(12) United States Patent
Kettenberger et al.

(10) Patent No.: US 10,418,126 B2
(45) Date of Patent: Sep. 17, 2019

(54) METHOD FOR IMPROVING ANTIBODY STABILITY

(71) Applicant: Hoffmann-La Roche Inc., Little Falls, NJ (US)

(72) Inventors: Hubert Kettenberger, Munich (DE); Stefan Klostermann, Neuried (DE); Florian Lipsmeier, Penzberg (DE); Apollon Papadimitriou, Bichl (DE); Jasmin Sydow-Andersen, Frederiksberg (DK)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 15/061,130

(22) Filed: Mar. 4, 2016

(65) Prior Publication Data

US 2016/0275238 A1 Sep. 22, 2016

Related U.S. Application Data

(63) Continuation of application No. PCT/EP2014/068649, filed on Sep. 3, 2014.

(30) Foreign Application Priority Data

Sep. 6, 2013 (EP) ..................................... 13183389
Sep. 12, 2013 (EP) ..................................... 13184174

(51) Int. Cl.
G16B 15/00 (2019.01)
G01N 33/68 (2006.01)
C07K 16/10 (2006.01)
C07K 16/22 (2006.01)
G16C 99/00 (2019.01)

(52) U.S. Cl.
CPC .............. G16B 15/00 (2019.02); C07K 16/10 (2013.01); C07K 16/22 (2013.01); G01N 33/6854 (2013.01); G16C 99/00 (2019.02); C07K 2317/56 (2013.01); C07K 2317/94 (2013.01); G01N 2500/00 (2013.01)

(58) Field of Classification Search
CPC ......................... G16B 15/00; G01N 33/6854
USPC ....................................................... 424/133.1
See application file for complete search history.

(56) References Cited

U.S. PATENT DOCUMENTS

| 8,278,262 B2 * | 10/2012 | Kolmar | A61K 38/56 435/7.21 |
| 9,598,682 B2 * | 3/2017 | Callewaert | |
| 2009/0130692 A1 * | 5/2009 | Kolmar | A61K 38/56 435/7.21 |
| 2017/0101635 A1 * | 4/2017 | Lavigne | C12P 19/14 |
| 2017/0175098 A1 * | 6/2017 | Pedersen | C12N 9/54 |
| 2017/0227547 A1 * | 8/2017 | Emrich | G01N 33/6854 |

OTHER PUBLICATIONS

Zhang et al Anal. Chem., 86, 3468-3475, Mar. 5, 2014.*
Sydow et al. PLOS One 9(6): e100736. doi:10.1371/journal.pone. 0100736, Jun. 2014.*
Jarasch et al. Journal of Pharmaceutical Sciences 104:1885-1898, 2015.*
Alsenaidy et al. J Pharm Sci. Jun. 2014 ; 103(6): 1613-1627. doi:10.1002/jps.23975.*
Sali (URL http://salilab.org/modeller/ (Jun. 12, 2009) pp. 1-272).*
Accelrys Inc. Launches Pipeline Pilot 8.0 (pp. 1-5; Mar. 27, 2018).*
Spassov et al. (Protein Engineering, Design & Selection vol. 21 No. 2 pp. 91-100, 2008).*
European Search Report issued in European Patent Application No. 13183389, dated May 22, 2014, in 10 pages.
International Preliminary Report on Patentability issued in International Application No. PCT/EP2014/068649, dated Mar. 8, 2016, in 11 pages.
Clarke et al., "Propensity for spontaneous succinimide formation from aspartyl and asparaginyl residues in cellular proteins", Int. J. Peptide Protein Res. 30:808-821 (1987).
International Search Report issued in International Application No. PCT/EP2014/068649, dated Jan. 7, 2015, in 4 pages.
Kosky et al., "Multivariate Analysis of the Sequence Dependence of Asparagine Deamidation Rates in Peptides", Pharmaceutical Research 26(11):2417-2428 (2009).
Kossiakoff, A.A., "Tertiary Structure is a Principal Determinant to Protein Deamidation", Science 240:191-194 (1988).
Wakankar et al., "Asparate Isomerization in the Complementarity-Determining Regions of Two Closely Related Monoclonal Antibodies", Biochemistry 46(6):1534-1544 (2007).
Bibov, M.Y. et al. (2004). "Influence of Nonferromentative Postranslation Desamidation of the Intensity of the Proteins of the Preparation Immune Lacquer," *Natural Sciences* 1:56-59. (English Translation Abstract Only).
Robinson, N.E. et al. (Apr. 10, 2001). "Prediction of Protein Deamidation Rates From Primary and Three-Dimensional Structure," *Proc. Natl. Acad. Sci. USA* 98(8):4367-4372.
Robinson, N.E. (Apr. 16, 2002). "Protein Deamidation," *Proc. Natl. Acad. Sci. USA* 99(8):5283-5288.
Wakankar, A.A. et al. (Nov. 2006). "Formulation Considerations for Proteins Susceptible to Asparagine Deamidation and Aspartate Isomerization," *J. Pharm. Sci.* 95(11):2321-2336.
Al-Lazikani, B. et al. (1997). "Standard Conformations for the Canonical Structures of Immunoglobulins," *J. Mol. Biol.* 273:927-948.

(Continued)

*Primary Examiner* — Lynn A Bristol
(74) *Attorney, Agent, or Firm* — Morrison & Foerster LLP

(57) ABSTRACT

Herein is reported a method for selecting or deselecting an antibody comprising a) determining for each Asp and Asn residue in an antibody Fv region the conformational flexibility of the $C_\alpha$-atom using a homology model ensemble, b) determining for each Asp and Asn residue in an antibody Fv region the size of the amino acid residue C-terminal to the Asp or Asn residue, and c) selecting an antibody in which the $C_\alpha$-atom is conformationally inflexible and/or the Asp or Asn has a big C-terminal amino acid residue, or deselecting an antibody in which the $C_\alpha$-atom has a moderate to high conformational flexibility and/or the Asp or Asn has a small C-terminal amino acid residue.

6 Claims, 8 Drawing Sheets

(56) References Cited

OTHER PUBLICATIONS

Athmer, L. et al. (Jun. 14, 2002). "The Influence of Protein Structure on the Products Emerging from Succinimide Hydrolysis," *J. Biol. Chem.* 277:30502-30507.

Bischoff, R. et al. (Dec. 9, 1994). "Deamidation of Asparagine and Glutamine Residues in Proteins and Peptides: Structural Determinants and Analytical Methodology," *J. Chromatogr. B Biomed. Appl.* 662(2):261-278.

Böhme, L. et al. (Aug. 2008). "Isoaspartate-containing Amyloid Precursor Protein-Derived Peptides Alter Efficacy and Specificity of Potential β-Secretases," *Biol. Chem.* 389(8):1055-1066.

Böhme, L. et al. (Aug. 2008). "Isoaspartate Residues Dramatically Influence Substrate Recognition and Turnover by Proteases," *Biol. Chem.* 389(8):1043-1053.

Brennan, T.V. et al. (1993). "Spontaneous Degradation of Polypeptides at Aspartyl and Asparaginyl Residues: Effects of the Solvent Dielectric," *Protein Sci.* 2:331-338.

Brennan, T.V. et al. (Jun. 1995). "Effect of Adjacent Histidine and Cysteine Residues on the Spontaneous Degradation of Asparaginyl- and Aspartyl-Containing Peptides," *Int. J. Pept. Protein Res.* 45(6):547-553.

Cacia, J. et al. (1996). "Isomerization of an Aspartic Acid Residue in the Complementarity-Determining Regions of a Recombinant Antibody to Human IgE: Identification and Effect on Binding Affinity," *Biochemistry* 35(6):1897-1903.

Capasso, S. et al. (Nov.-Dec. 1992). "Conformation of Aminosuccinyl Dipeptides Ac-L-X-L-Asu-NMe From Empirical Energy Calculations," *Pept. Res.* 5(6):325-330.

Capasso, S. (Mar. 2000). "Estimation of the Deamidation Rate of Asparagine Side Chains," *J. Pept. Res.* 55(3):224-229.

Catak, S. et al. (Feb. 12, 2009, e-pub. Jan. 16, 2009). "Deamidation of Asparagine Residues: Direct Hydrolysis Versus Succinimide-Mediated Deamidation Mechanisms," *J. Phys. Chem. A* 113(6):1111-1120.

Chelius, D. et al. (Sep. 15, 2005, e-pub. Aug. 18, 2005). "Identification and Characterization of Deamidation Sites in the Conserved Regions of Human Immunoglobulin Gamma Antibodies," *Anal. Chem.* 77(18):6004-6011.

Chennamsetty, N. et al. (Jul. 21, 2009). "Design of Therapeutic Proteins With Enhanced Stability," *Proc. Natl. Acad. Sci. USA* 106(29):11937-11942.

Chothia, C. et al. (Dec. 21/28, 1989). "Conformations of Immunoglobulin Hypervariable Regions," *Nature* 342:877-883.

Chu, G.C. et al. (Jun. 2007, e-pub. Mar. 24, 2007). "Accumulation of Succinimide in a Recombinant Monoclonal Antibody in Mildly Acidic Buffers Under Elevated Temperatures," *Pharm. Res.* 24(6):1145-1156.

Deverman, B.E. et al. (Oct. 4, 2002). "Bcl-$x_L$ Deamidation is a Critical Switch in the Regulation of the Response to DNA Damage," *Cell* 111:51-62.

Diepold, K. et al. (Jan. 17, 2012). "Simultaneous Assessment of Asp Isomerization and Asn Deamidation in Recombinant Antibodies by LC-MS following Incubation at Elevated Temperatures," *PloS One.* 7(1): e30295, 11 pages.

Dimitriadou, E. et al. (Feb. 2, 2017). "Misc. Functions of the Department of Statistics, Probability Theory Group (Formerly:E1071)," retrieved from <http://CRAN.R-project.org/package=e1071/index.html> last visited Jul. 24, 2018, 2 pages . . . .

Geiger, T. et al. (Jan. 15, 1987). "Deamidation, Isomerization, and Racemization at Asparaginyl and Aspartyl Residues in Peptides," *J. Biol. Chem.* 262(2):785-794.

Hambly, D.M. et al. (Sep. 1, 2009). "Detection and Quantitation of IgG 1 Hinge Aspartate Isomerization: A Rapid Degradation in Stressed Stability Studies," *Anal. Chem.* 81(17):7454-7459.

Harding, J.J. et al. (Oct. 1989). "Non-Enzymic Post-Translational Modification of Proteins in Aging. A Review," *Mech. Ageing Dev.* 50(1):7-16.

Harris, R.J. et al. (2001). "Identification of Multiple Sources of Charge Heterogeneity in a Recombinant Antibody," *J. Chromatogr. B Biomed.* 752:233-245.

Huang, L. et al. (Mar. 1, 2005, e-pub. Jan. 22, 2005). "In Vivo Deamidation Characterization of Monoclonal Antibody by LC/MS/MS," *Anal. Chem.* 77(5):1432-1439.

Joshi, A.B. et al. (Sep. 2005). "Studies on the Mechanism of Aspartic Acid Cleavage and Glutamine Deamidation in the Acidic Degradation of Glucagon," *J. Pharm. Sci.* 94(9):1912-1927.

Karatzoglou, A. et al. (Nov. 2004). "kernlab—An S4 Package for Kernel Methods in R," *Journal of Statistical Software* 11(9):1-20.

Kosky, A.A. et al. (1999). "The Effects of Alpha-Helix on the Stability of Asn Residues: Deamidation Rates in Peptides of Varying Helicity," *Protein Sci.* 8:2519-2523.

Kosugi, S. et al. (Jun. 20, 2008, e-pub. Mar. 31, 2008). "Suppression of Protein L-Isoaspartyl (D-aspartyl) Methyltransferase Results in Hyperactivation of EGF-Stimulated MEK-ERK Signaling in Cultured Mammalian Cells," *Biochem. Biophys. Res. Commun.* 371(1):22-27.

Kroon, D.J. et al. (Nov. 1992). "Identification of Sites of Degradation in a Therapeutic Monoclonal Antibody by Peptide Mapping," *Pharm. Res.* 9(11):1386-1393.

Li, H. et al. (2005, e-pub. Oct. 17, 2005). "Very Fast Empirical Prediction and Rationalization of Proteni $pK_a$ Values," *Proteins* 61:704-721.

Liu, H. et al. (Jun. 6, 2006, e-pub. Apr. 27, 2006). "Characterization of the Stability of a Fully Human Monoclonal IgG After Prolonged Incubation at Elevated Temperature," *J. Chromatogr. B Analyt. Technol. Biomed. Life Sci.* 837(1-2):35-43.

Liu, H. et al. (Nov. 7, 2008, e-pub. Sep. 24, 2008). "Peptide Mapping With Liquid Chromatography Using a Basic Mobile Phase," *J. Chromatogr. A* 1210(1):76-83.

Manning, M.C. et al. (1989). "Stability of Protein Pharmaceuticals," *Pharm. Res.* 6(11):903-918.

Marti-Renom, M.A. et al. (2000). "Comparative Protein Structure Modeling of Genes and Genomes," *Annu. Rev. Biophys. Biomol. Struct.* 29:291-325.

Martin, A.C. (Nov. 15, 1996). "Structural families in Loops of Homologous Proteins: Automatic Classification, Modelling and Application to Antibodies," *J. Mol. Biol.* 263(5):800-815.

Morea, V. et al. (Jan. 16, 1998). "Conformations of the Third Hypervariable Region in the VH Domain of Immunoglobulins," *J. Mol. Biol.* 275(6):269-294.

Oliyai, C. et al. (Jan. 1993). "Chemical Pathways of Peptide Degradation. IV. Pathways, Kinetics, and Mechanism of Degradation of an Aspartyl Residue in a Model Hexapeptide," *Pharm. Res.* 10(1):95-102.

Oliyai, C. et al. (May 1994). "Chemical Pathways of Peptide Degradation. VI. Effect of the Primary Sequence on the Pathways of Degradation of Aspartyl Residues in Model Hexapeptides," *Pharm. Res.* 11(5):751-758.

Oliyai, C. et al. (Jun. 1994). "Chemical Pathways of Peptide Degradation. VII. Solid State Chemical Instability of an Aspartyl Residue in a Model Hexapeptide," *Pharm. Res.* 11(6):901-908.

Patel, K. et al. (Jul. 1990). "Chemical Pathways of Peptide Degradation. II. Kinetics of Deamidation of an Asparaginyl Residue in a Model Hexapeptide," *Pharm. Res.* 7(7):703-711.

Perkins, M. et al. (2000). "Determination of the Origin of Charge Heterogeneity in a Murine Monoclonal Antibody," *Pharm. Res.* 17(9):1110-1117.

Rehder, D.S. et al. (Feb. 26, 2008, e-pub. Jan. 31, 2008). "Isomerization of a Single Aspartyl Residue of Anti-Epidermal Growth Factor Receptor Immunoglobulin γ2 Antibody Highlights the Role Avidity Plays in Antibody Activity," *Biochemistry* 47(8):2518-2530.

Reichert, J.M. et al. (Sep. 2005). "Monoclonal Antibody Successes in the Clinic," *Nat. Biotechnol.* 23(9):1073-1078.

Ripley, B. (Mar. 17, 2018). "Classification and Regression Tress," retrieved from <http://CRAN.R-project.org/package/tree/index.html> last visited Jul. 24, 2017, 1 page.

Robinson, AB. Et al. (Jul. 1970). "Controlled Deamidation of Peptides and Proteins: An Experimental Hazard and a Possible Biological Timer," *Proc. Natl. Acad. Sci. USA* 66(3):753-757.

(56) References Cited

OTHER PUBLICATIONS

Robinson, N.E. et al. (Jan. 30, 2001). "Molecular Clocks," *Proc. Natl. Acad. Sci. USA* 98(3):944-949.
Robinson, N.E. et al. (Oct. 23, 2001). "Deamidation of Human Proteins," *Proc. Natl. Acad. Sci. USA* 98(22):12409-12413.
Sali, A. et al. (1993). "Comparative Protein Modelling by Satisfaction of Spatial Restraints," *J. Mol. Biol.* 234:779-815.
Shimizu, T. et al. (2005). "D-Amino Acid Biosystem: Biological Significance of Isoaspartate and Its Repair System," *Biol. Pharm. Bull.* 28(9):1590-1596.
Simpson, R.J. (2010). "Disruption of Cultured Cells by Nitrogen Cavitation," *Cold Spring Harb. Protoc.* pp. 1219-1222.
Sinha, S. et al. (2009, e-pub. May 28, 2009). "Effect of Protein Structure on Deamidation Rate in the Fc Fragment of an IgG1 Monoclonal Antibody," *Protein Sci.* 18:1573-1584.
Sreedhara, A. et al. (2012, e-pub. Aug. 2, 2011). "Characterization of the Isomerization Products of Aspartate Residues at Two Different Sites in a Monoclonal Antibody," *Pharm. Res.* 29:187-197.
Stephenson, R.C. et al. (Apr. 15, 1989). "Succinimide Formation from Aspartyl and AsparaginPyelp tides as a Model for the Spontaneous Degradation of Proteins," *J. Biol. Chem.* 264(11):6164-6170.
Swann, P.G. et al. (2008, e-pub. Jul. 2, 2008). "Considerations for the Development of Therapeutic Monoclonal Antibodies," *Curr. Opin. Immunol.* 20:493-499.
Takata, T. et al. (Jul. 31, 2007). "Deamidation Alters the Structure and Decreases the Stability of Human Lens βA3-Crystallin," *Biochemistry* 46(30):8861-8871, 28 pages.
Takata, T. et al. (2008). "Deamidation Destabilizes and Triggers Aggregation of a Lens Protein, βA3-Crystallin," *Protein Sci.* 17:1565-1575.
Themeau, R.M. et al. (Feb. 23, 2018). "Recursive Partitioning and Regression Trees," retrieved from <http://CRAN.R-project.org/packages/rpart/index.html> last visited Jul. 24, 2018, 2 pgs . . . .
Timm, V. et al. (Mar. 15, 2010, e-pub. Jan. 29, 2010). "Identification and Characterization of Oxidation and Deamidation Sites in Monoclonal Rat/Mouse Hybrid Antibodies," *J. Chromatogr. B Analyt. Technol. Biomed. Life Sci.* 878(9-10):777-784.
Tomizawa, H. et al. (Jul. 26, 1994). "Isolation and Characterization of 101-succinimide Lysozyme That Possesses the Cyclic Imide at Asp101-Gly102," *Biochemistry* 33(29):8770-8774.
Tyler-Cross, R. et al. (Nov. 25, 1991). "Effects of Amino Acid Sequence, Buffers, and Ionic Strength on the Rate and Mechanism of Deamidation of Asparagine Residues in Small Peptide," *J. Biol. Chem.* 266(33):22549-22556.
Valliere-Douglass, J. et al. (May 1, 2008, e-pub. Mar. 21, 2008). "Separation and Characterization of an IgG2 antibody Containing a Cyclic Imide in CDR1 of Light Chain by Hydrophobic Interaction Chromatography and Mass Spectrometry," *Anal. Chem.* 80(9):3168-3174.
Venables, W.N. et al. (Mar. 15, 2002). "Modem Applied Statistics with S," 4th ed. (Springer, New York.), 8 pages.
Vlasak, J. et al. (2008). "Heterogeneity of Monoclonal Antibodies Revealed by Charge-Sensitive Methods," *Curr. Pharm. Biotechnol.* 9(6):468-481.
Vlasak, J. et al. (2009, e-pub. Jun. 2, 2009). "Identification and Characterization of Asparagine Deamidation in the Light Chain CDR1 of a Humanized IgG1 Antibody," *Anal. Biochem.* 392:145-154.
Wakankar, A.A. et al. (Jul. 2007). "The Effect of Cosolutes on the Isomerization of Aspartic Acid Residues and Conformational Stability in a Monoclonal Antibody," *J. Pharm. Sci.* 96(7):1708-1718.

Weihs, C. et al. (2005). "klaR Analyzing German Business Cycles," in *Data Analysis and Decision*, eds. Baier, D., Decker, R., & Schmidt-Thieme, L. (Springer-Verlag, Berlin), pp. 335-343.
Weintraub, S.J. et al. (2004). "Asparagine Deamidation: A Regulatory Hourglass," *Mech. Ageing Dev.* 125:255-257.
Weintraub, S.J. et al. (Oct. 23, 2007). "Chronoregulation by Asparagine Deamidation," *Sci. STKE* 409:Re7, 6 pages.
Whitelegg, N. et al. (2004). "Antibody Variable Regions: Toward a Unified Modeling Method," *Methods Mol. Biol.* 248:51-91.
Wright, H.T. (1991). "Nonenzymatic Deamidation of Asparaginyl and Glutaminyl Residues in Proteins," *Crit. Rev. Biochem. Mol. Biol.* 26(1):1-52.
Wright, H.T. (Feb. 1991). "Sequence and Structure Determinants of the Nonenzymatic Deamidation of Asparagine and Glutamine Residues in Proteins," *Protein Eng.* 4(3):283-294.
Xiao, G., et al. (Apr. 1, 2007, e-pub. Feb. 22, 2007). "$^{18}$O Labeling Method for Identification and Quantification of Succinimide in Proteins," *Anal. Chem.* 79(7):2714-2721.
Xiao, G. et al. (May 12, 2008, Dec. 14, 2007). "Identification and Quantification of Degradations in the Asp-Asp Motifs of a Recombinant Monoclonal Antibody," *J. Pharm. Biomed. Anal.* 47(1):23-30.
Xie, M. et al. (Jan. 1999, e-pub. Nov. 6, 1998). "Secondary Structure and Protein Deamidation," *J. Pharm. Sci.* 88(1):8-13.
Xie, M. et al. (Sep. 2000). "Reactivity toward Deamidation of Asparagine Residues in Beta-Turn Structures," *J. Pept. Res.* 56(3):165-171.
Yan, B. et al. (Oct. 2009). "Succinimide Formation at Asn 55 in the Complementarity Determining Region of a Recombinant Monoclonal Antibody IgG1 Heavy Chain," *J. Pharm. Sci.* 98(10):3509-3521.
Yi, L. et al. (Mar. 2013, e-pub. Dec. 20, 2012). "Isomerization of Asp-Asp Motif in Model Peptides and a Monoclonal Antibody Fab Fragment," *J. Pharm. Sci.* 102(3):947-959.
Yu, X.C. et al. (2011). "Accurate Determination of Succinimide Degradation Products Using High Fidelity Trypsin Digestion Peptide map Analysis," *Anal. Chem.* 83:5912-5919.
Zabrouskov, V. et al. (Jan. 24, 2006). "Stepwise Deamidation of Ribonuclease A at Five Sites Determined by Top Down Mass Spectrometry," *Biochemistry* 45(3):987-992, 13 pages.
Zhang, W. et al. (Jan. 2003). "Analysis of Isoaspartate in a Recombinant Monoclonal Antibody and Its Charge Isoforms," *J. Pharm. Biomed. Anal.* 30(5):1479-1490.
Zhang, J. et al. (Mar. 2011, e-pub. Dec. 2, 2010). "Identification of Isomerization and Racemization of Aspartate in the Asp-Asp Motifs of a Therapeutic Protein," *Anal. Biochem.* 410(2):234-243.
Zhao, R. et al. (Jan. 2004). "An Oncogenic Tyrosine Kinase Inhibits DNA Repair and DNA-Damage-Induced Bcl-$x_L$ Deamidation in T Cell Transformation," *Cancer Cell* 5:37-49.
Zhao, R. et al. (Jan. 2007). "DNA Damage-Induced Bcl-xL Deamidation is Mediated by NHE-1 Antiport Regulated Intracellular pH," *PloS Biol.* 5(1):e1, 15 pages.
Zheng, J.Y. et al. J. (2006, e-pub. Nov. 28, 2005). "Influence of pH, Buffer Species, and Storage Temperature on Physicochemical Stability of a Humanized Monoclonal Antibody LA298," *Int. J. Pharm.* 308:46-51.
Written Opinion of the International Searching Authority, dated Jan. 1, 2015, for PCT Application No. PCT/EP2014/068649, filed Sep. 3, 2014, 10 pages.
Capasso. S. et al. (Nov. 1999). "Effect of the Three-Dimensional Structure on the Deamidation Reaction of Ribonuclease A," *J. Peptide Res.* 54(5):377-382.
Notice of Reasons for Rejection, dated Sep. 5, 2018, for Japanese Patent Application No. 2016-539511, 3 pages.

\* cited by examiner

METHOD FOR IMPROVING ANTIBODY STABILITY

CROSS REFERENCE TO RELATED APPLICATIONS

This application is a continuation of International Patent Application No. PCT/EP2014/068649, filed on Sep. 3, 2014, which claims priority to European Patent Application Nos. 13183389.9, filed on Sep. 6, 2013, and 13184174.4, filed on Sep. 12, 2013, the entire contents of which are incorporated herein by reference.

Herein is reported a method for improving antibody stability with respect to the identification and removal of asparagine and aspartate degradation sites in antibody amino acid sequences based on a structure-based approach.

BACKGROUND OF THE INVENTION

Monoclonal antibodies and antibody domain-based molecules constitute the majority of protein therapeutics under clinical investigation (1, 2). Monoclonal antibodies are potent in a diverse range of therapeutic indications, and are easily generated. The specificity of the antibody is primarily determined by sequences in the CDRs located in the variable domain. The process of selecting a clinical candidate starts with screening for functional properties of a large number of monoclonal antibodies. Screening is followed by detailed in vitro profiling of up to hundreds of molecules to identify a monoclonal antibody that fulfills all desired functional criteria and additionally displays chemical and biophysical stability. Hence, monoclonal antibodies with instability issues that can affect their structure and biological function have to be identified and deselected to avoid unwanted degradation during manufacturing and storage, and in vivo after application.

One degradation reaction occurring in proteins is the chemical degradation of asparagine (Asn) (3) and aspartate (Asp) residues (4, 5). These reactions may be kept under control by appropriate formulation conditions (6-9). If Asn and Asp residues are involved in antigen recognition, their chemical alteration can lead to a reduction of potency of the antibody (10-14).

Diverse parameters were proposed which may influence the degradation propensity of Asn and Asp residues, e.g. the primary sequence (3, 5, 16, 33, 40, 51-56), the solvent dielectric constant, temperature, and the pH, mostly in the peptide (52, 53, 57-59), but also in the protein context (7, 10, 35, 60). Already in the 1980s, several structural requirements were suggested as principal determinants for protein deamidation (5, 61) which have later been confirmed and extended (34, 37, 38, 40, 46, 51, 62-64).

Despite accumulated knowledge about the degradation mechanism and its environmental requirements, spontaneous deamidation and isomerization in monoclonal antibodies remains an unresolved issue.

SUMMARY OF THE INVENTION

Herein is reported a correlation between the degradation of Asp and Asn residues in polypeptides and a set of structural parameters. It has been found that degradation hot-spots can be characterized by (i) their conformational flexibility, (ii) the size of the C-terminally flanking amino acid residue, and (iii) secondary structural parameters. Using these parameters, a prediction method for the degradation propensity of Asn and Asp residues has been established.

One aspect as reported herein is a method for selecting an antibody with degradation (=modification) stability comprising the following steps
a) determining for each Asp and Asn residue in an antibody Fv region the conformational flexibility of the $C_\alpha$-atom with/in/using a homology model ensemble,
b) determining for each Asp and Asn residue in an antibody Fv region the size of the amino acid residue directly C-terminal to the Asp or Asn residue,
c) selecting an antibody in which the $C_\alpha$-atom is conformationally inflexible and/or the Asp or Asn residue has a big C-terminal amino acid residue.

One aspect as reported herein is a method for selecting one or more antibodies with degradation (=modification) stability comprising the following steps
a) providing two or more antibodies,
b) determining for each Asp and Asn residue in an antibody Fv region the conformational flexibility of the $C_\alpha$-atom with/in/using a homology model ensemble,
c) determining for each Asp and Asn residue in an antibody Fv region the size of the amino acid residue directly C-terminal to the Asp or Asn residue,
d) selecting one or more antibodies in which the $C_\alpha$-atom is conformationally inflexible and/or the Asp or Asn residue has a big C-terminal amino acid residue,
and thereby selecting one or more antibodies with degradation (=modification) stability.

One aspect as reported herein is a method for deselecting (=selecting for removal from a multitude of antibodies) an antibody comprising the following steps
a) determining for each Asp and Asn residue in an antibody Fv region (of a multitude of antibody Fv regions) the conformational flexibility of the $C_\alpha$-atom with/in/using a homology model ensemble,
b) determining for each Asp and Asn residue in an antibody Fv region the size of the amino acid residue directly C-terminal to the Asp or Asn residue,
c) deselecting/removing (from the multitude of antibody Fv regions) an antibody in which the $C_\alpha$-atom has a moderate to high conformational flexibility and/or the Asp or Asn residue has a small C-terminal amino acid residue.

One aspect as reported herein is a method for deselecting (=selecting for removal from a multitude of antibodies) one or more antibodies comprising the following steps
a) providing two or more antibodies,
b) determining for each Asp and Asn residue in an antibody Fv region (of a multitude of antibody Fv regions) the conformational flexibility of the $C_\alpha$-atom with/in/using a homology model ensemble,
c) determining for each Asp and Asn residue in an antibody Fv region the size of the amino acid residue directly C-terminal to the Asp or Asn residue,
d) deselecting/removing (from the multitude of antibody Fv regions) one or more antibodies in which the $C_\alpha$-atom has a moderate to high conformational flexibility and/or the Asp or Asn residue has a small C-terminal amino acid residue.

One aspect as reported herein is a method for identifying or deselecting an antibody that is prone to asparagine (Asn) degradation (deamidation and/or succinimide-formation) comprising the following steps
a) determining for each Asn residue in an antibody Fv region the conformational flexibility of the $C_\alpha$-atom with/in/using a homology model ensemble, b) determining for each Asn residue in an antibody Fv region that has a small C-terminal amino acid residue the backbone dihedral angle phi, c) determining for each Asn residue in an antibody Fv region that has a small C-terminal amino acid residue and a backbone dihedral angle phi of more than −75.2 degrees the solvent exposure and the occurrence/presence of a change in the secondary structure N-terminally to the Asn residue and the distance in amino acid residues of the occurrence of this change relative to the Asn residue, and d) identifying or deselecting an antibody that is prone to asparagine (Asn) degradation (deamidation and/or succinimide-formation) if
  i) the Asn residue is in CDR loop 1, its $C_\alpha$-atom is conformationally flexible and the C-terminal amino acid residue is Asp, Pro, Thr or Asn,
  ii) the $C_\alpha$-atom of the Asn is conformationally flexible, has a backbone dihedral angle phi of less than −75.2 degrees, and the amino acid residue C-terminal to the Asn residue is small, or
  iii) the $C_\alpha$-atom of the Asn residue is conformationally flexible, has a backbone dihedral angle phi of more than −75.2 degrees, has a high solvent exposure, and a change in amino-terminal secondary structure occurs within a stretch of more than 3 amino acid residues relative to the Asn residue.

One aspect as reported herein is a method for identifying or deselecting one or more antibodies that are prone to asparagine (Asn) degradation (deamidation and/or succinimide-formation) comprising the following steps a) providing two or more antibodies, b) determining for each Asn residue in an antibody Fv region the conformational flexibility of the $C_\alpha$-atom with/in/using a homology model ensemble, c) determining for each Asn residue in an antibody Fv region that has a small C-terminal amino acid residue the backbone dihedral angle phi, d) determining for each Asn residue in an antibody Fv region that has a small C-terminal amino acid residue and a backbone dihedral angle phi of more than −75.2 degrees the solvent exposure and the occurrence/presence of a change in the secondary structure N-terminally to the Asn residue and the distance in amino acid residues of the occurrence of this change relative to the Asn residue, and e) identifying or deselecting one or more antibodies that are prone to asparagine (Asn) degradation (deamidation and/or succinimide-formation) if
  i) the Asn residue is in CDR loop 1, its $C_\alpha$-atom is conformationally flexible and the C-terminal amino acid residue is Asp, Pro, Thr or Asn,
  ii) the $C_\alpha$-atom of the Asn is conformationally flexible, has a backbone dihedral angle phi of less than −75.2 degrees, and the amino acid residue C-terminal to the Asn residue is small, or
  iii) the $C_\alpha$-atom of the Asn residue is conformationally flexible, has a backbone dihedral angle phi of more than −75.2 degrees, has a high solvent exposure, and a change in amino-terminal secondary structure occurs within a stretch of more than 3 amino acid residues relative to the Asn residue.

One aspect as reported herein is a method for selecting one or more antibodies with improved asparagine (Asn) stability (reduced deamidation and/or succinimide-formation) comprising the following steps a) providing two or more antibodies, b) determining for each Asn residue in each antibody Fv region the conformational flexibility of the $C_\alpha$-atom with/in/using a homology model ensemble, c) determining the backbone dihedral angle phi for each Asn residue in each antibody Fv region which has a small C-terminal amino acid residue, d) determining the solvent exposure and the occurrence/presence of a change in the secondary structure N-terminally to the Asn residue and the distance in amino acid residues of the occurrence of this change to the Asn residue, for each Asn residue with a small C-terminal amino acid residue and a backbone dihedral angle phi of more than −75.2 degrees in each antibody Fv region, and e) removing/deleting/deselecting from the two or more antibodies those antibodies that have at least one of the following:
  i) an Asn residue in CDR loop 1 that has a $C_\alpha$-atom that has conformational flexibility and that has Asp, Pro, Thr or Asn as C-terminal amino acid residue,
  ii) an Asn residue that has a conformationally flexible $C_\alpha$-atom, a backbone dihedral angle phi of less than −75.2 degrees, and that has a small C-terminal amino acid residue, or
  iii) an Asn residue that has a conformationally flexible $C_\alpha$-atom, that has a backbone dihedral angle phi of more than −75.2 degrees, that has a high solvent exposure, and a change in amino-terminal secondary structure occurs within a stretch of more than 3 amino acid residues of the Asn residue and thereby selecting one or more antibodies with improved asparagine (Asn) stability.

One aspect as reported herein is a method for obtaining an antibody with reduced asparagine (Asn) degradation (deamidation and/or succinimide-formation), comprising one or more of the following steps reducing the conformational flexibility of the $C_\alpha$-atom, increasing the size of the amino acid residue C-terminal to the Asn residue.

One aspect as reported herein is a method for identifying or deselecting an antibody that is prone to aspartate (Asp) degradation (isomerization and/or succinimide-formation) comprising the following steps:

a) determining for each Asp residue in an antibody Fv region the conformational flexibility of the $C_\alpha$-atom with/in/using a homology model ensemble, b) determining for each Asp residue in an antibody Fv region the size of the amino acid residue C-terminally to the Asp residue, c) determining for each Asp residue in an antibody Fv region the occurrence/presence of a change in the secondary structure C-terminally to the Asp residue and the distance in amino acid residues of the occurrence of the change to the Asp residue, and d) identifying or deselecting the antibody that is prone to Asp degradation (isomerization and/or succinimide-formation) if
  i) the $C_\alpha$-atom of the Asp residue has high conformational flexibility and the amino acid residue C-terminal to the Asp residue is small, or
  ii) the $C_\alpha$-atom of the Asp residue has moderate conformational flexibility, the amino acid residue to the Asp residue is small, and a change in carboxy-terminal secondary structure occurs within a stretch of less than 3 amino acid residues relative to the Asp residue, or iii) the $C_\alpha$-atom of the Asp residue has moderate conformational flexibility, the amino acid residue C-terminal to the Asp residue is a Gly residue, and a change in carboxy-terminal secondary structure occurs at a distance of more than 3 amino acid residues relative to the Asp residue.

One aspect as reported herein is a method for identifying or deselecting one or more antibodies that are prone to aspartate (Asp) degradation (isomerization and/or succinimide-formation) comprising the following steps:
a) providing two or more antibodies,
b) determining for each Asp residue in an antibody Fv region the conformational flexibility of the $C_\alpha$-atom with/in/using a homology model ensemble,
c) determining for each Asp residue in an antibody Fv region the size of the amino acid residue C-terminally to the Asp residue,
d) determining for each Asp residue in an antibody Fv region the occurrence/presence of a change in the secondary structure C-terminally to the Asp residue and the distance in amino acid residues of the occurrence of the change to the Asp residue, and
e) identifying or deselecting one or more antibodies that are prone to Asp degradation (isomerization and/or succinimide-formation) if
   i) the $C_\alpha$-atom of the Asp residue has high conformational flexibility and the amino acid residue C-terminal to the Asp residue is small, or
   ii) the $C_\alpha$-atom of the Asp residue has moderate conformational flexibility, the amino acid residue to the Asp residue is small, and a change in carboxy-terminal secondary structure occurs within a stretch of less than 3 amino acid residues relative to the Asp residue, or
   iii) the $C_\alpha$-atom of the Asp residue has moderate conformational flexibility, the amino acid residue C-terminal to the Asp residue is a Gly residue, and a change in carboxy-terminal secondary structure occurs at a distance of more than 3 amino acid residues relative to the Asp residue.

One aspect as reported herein is a method for selecting one or more antibodies with improved aspartate (Asp) stability (reduced isomerization and/or succinimide-formation) comprising the following steps:
a) providing two or more antibodies,
b) determining for each Asp residue in each antibody Fv region the conformational flexibility of the $C_\alpha$-atom with/in/using a homology model ensemble,
c) determining for each Asp residue in each antibody Fv region the size of the amino acid residue C-terminally to the Asp residue,
d) determining for each Asp residue in each antibody Fv region the occurrence/presence of a change in the secondary structure C-terminally to the Asp residue and the distance in amino acid residues of the occurrence of this change relative to the Asp residue, and
e) removing/deleting/deselecting from the two or more antibodies those antibodies that have at least one of the following:
   i) an Asp residue with a conformationally flexible $C_\alpha$-atom and that has a small C-terminal amino acid residue,
   ii) an Asp residue that has a $C_\alpha$-atom that has moderate conformational flexibility, that has a small C-terminal amino acid, and a change in carboxy-terminal secondary structure occurs within a stretch of less than 3 amino acid residues of the Asp residue, or
   iii) an Asp residue that has a $C_\alpha$-atom that has moderate conformational flexibility, that has Gly as C-terminal amino acid residue, and a change in carboxy-terminal secondary structure occurs at a distance of more than 3 amino acid residues of the Asp residue,
and thereby selecting one or more antibodies with improved aspartate (Asp) stability.

One aspect as reported herein is a method for obtaining an antibody with reduced aspartate (Asp) degradation (isomerization and/or succinimide-formation), comprising one or both of the following steps:
reducing the conformational flexibility of the $C_\alpha$-atom,
increasing the size of the amino acid residue C-terminal to the Asp residue.

In one embodiment the amino acid residue C-terminal to the Asp residue is changed to a big amino acid residue.

One aspect as reported herein is a method for selecting an antibody with long term storage stability comprising the following steps
a) determining for each Asp and Asn residue in an antibody Fv region the conformational flexibility of the $C_\alpha$-atom with/in/using a homology model ensemble,
b) determining for each Asp and Asn residue in an antibody Fv region the size of the amino acid residue C-terminal to the Asp or Asn residue,
c) selecting an antibody in which the $C_\alpha$-atom is conformationally inflexible and/or the Asp or Asn has a big C-terminal amino acid residue.

One aspect as reported herein is a method for selecting one or more antibodies with long term storage stability comprising the following steps
a) providing two or more antibodies,
b) determining for each Asp and Asn residue in an antibody Fv region the conformational flexibility of the $C_\alpha$-atom with/in/using a homology model ensemble,
c) determining for each Asp and Asn residue in an antibody Fv region the size of the amino acid residue C-terminal to the Asp or Asn residue,
d) selecting an antibody in which the $C_\alpha$-atom is conformationally inflexible and/or the Asp or Asn has a big C-terminal amino acid residue,
and thereby selecting one or more antibodies with long term storage stability.

One aspect as reported herein is a method for producing an antibody comprising the following steps:
a) cultivating a mammalian cell comprising a nucleic acid encoding an antibody that has been selected with a method as reported herein, or that has been obtained with a method as reported herein,
b) recovering the antibody from the cell or the cultivation medium and thereby producing the antibody.

One aspect as reported herein is a method for producing an antibody comprising the following steps:
a) cultivating a mammalian cell comprising a nucleic acid encoding an antibody that has been selected with a method as reported herein,
b) recovering the antibody from the cell or the cultivation medium and thereby producing the antibody.

In the following embodiments of all aspects as reported herein are given. It is expressly stated that any combination of individual embodiments is also encompassed by this listing.

In one embodiment the conformational flexibility is the root mean square deviation (RMSD) of the respective Asn/Asp residues' Cα-atoms in a homology model ensemble. In one embodiment the homology model ensemble is an ensemble (set of 5).

In one embodiment i) conformational inflexible is a RMSD of 0.01 Å or less, ii) conformational flexible is a RMSD of more than 0.01 Å, iii) moderate conformational flexibility is a RMSD between 0.145 Å and 0.485 Å, and iv) high conformational flexibility is a RMSD of more than 0.485 Å.

In one embodiment the homology model ensemble is made with the antibody Fv fragment.

In one embodiment a small amino acid residue is Gly, Ala, Ser, Cys or Asp. In one embodiment a small amino acid residue is Gly, Ala, Ser or Cys.

In one embodiment the method comprises the further step: providing the amino acid sequence of an antibody Fv region.

In one embodiment high solvent exposure is a SASA value of more than 89.4 Å$^2$.

In one embodiment a uniform experimental mass spectrometrical data set is used for generating the homology model ensemble.

In one embodiment all CDRs are subjected to a loop modeling procedure, yielding a five-membered homology model ensemble.

In one embodiment the method does not require molecular dynamics simulations.

In one embodiment a residue counts as a degradation spot if at least one member of the five-membered ensemble was classified as such.

In one embodiment a Pipeline Pilot implementation of a single-tree lookahead-enabled recursive partitioning algorithm is used.

In one embodiment the succeeding backbone nitrogen's solvent accessible surface area was determined computationally and the number of hydrogen bonds was counted.

In one embodiment the transition state-like conformation was probed by measuring the distance of the side chain $C_\gamma$-atom to the $N_{n+1}$-atom, the side chain dihedral angle •1, and the dihedral angle CGONC that was defined as the angle between the atoms $C_\gamma$, O, $N_{n+1}$, and C.

In one embodiment the solvent-accessible surface area of each Asp or Asn was determined.

In one embodiment the C-terminal (successor) amino acid size and the backbone dihedral angles φ ($C'_{n-1}$—N—$C_\alpha$—C') and ψ (N—$C_\alpha$—C'—$N_{n+1}$) are determined.

In one embodiment the root mean square deviation (RMSD) of the Asn/Asp residues' $C_\alpha$-atoms in the homology model ensemble (set of 5) reflects structural diversity within the ensemble and is seen as an indication of possible conformational flexibility.

In one embodiment the secondary structure element (the residue is embedded in helix, sheet, turn, or coil), and the distance to the next different N- and C-terminal secondary structure element are included as parameters.

In one embodiment the distance between the $C_\alpha$-atoms of the n−1 and the n+1 residue is determined.

DETAILED DESCRIPTION OF THE INVENTION

Monoclonal antibodies are the most promising protein therapeutics in diverse indication areas. Standard approaches for monoclonal antibody generation always lead to several suitable candidates. From these candidates, monoclonal antibodies with high therapeutic potency that are chemically stable have to be selected, to avoid degradation during manufacturing, storage, and in vivo. Antibodies are frequently degraded by asparagine (Asn) deamidation and aspartate (Asp) isomerization.

Asn and Asp residues share a common degradation pathway that precedes via the formation of a cyclic succinimide intermediate (FIG. 1) (3, 5, 33). Succinimide formation results from an intramolecular rearrangement after deamidation of Asn or dehydration of Asp by nucleophilic attack of the backbone nitrogen of the succeeding amino acid on the Asn/Asp side chain γ-carbonyl group. The metastable cyclic imide can hydrolyze at either one of its two carbonyl groups to form aspartyl or iso-aspartyl linkages in different ratios, depending on hydrolysis conditions and conformational restraints (3, 5, 20, 34-36). In addition, alternative degradation mechanisms were proposed (10) such as nucleophilic attack by the backbone carbonyl oxygen to form a cyclic isoimide (5, 37, 38) or direct water-assisted hydrolysis of Asn to Asp (39, 40). Several analytical methods, mostly charge-sensitive methods such as ion exchange chromatography or isoelectric focusing, were described to detect either of the degradation products, i.e. succinimide, Asp or isoAsp (13, 41, 42). Most suitable for the quantification and the localization of degradation sites in proteins is the analysis via liquid chromatography tandem mass spectrometry (LC-MS/MS) (12, 13, 38, 43-50).

Based on a uniform experimental mass spectrometrical data set of site-specific degradation events in 37 monoclonal antibodies, combined with structural parameters derived from homology models, the parameters contributing to and their respective contribution in the degradation pathway have been identified. A method has been developed for the identification and selection of chemically stable monoclonal antibodies.

The term "homology model" denotes a three-dimensional model of an amino acid sequence that has been obtained by constructing a three-dimensional model, in one embodiment a three-dimensional atomic-resolution model, of the amino acid sequence in question based on an experimentally-determined reference structure of a related homologous amino acid sequence. The generation of the homology model is based on the determination of (general) sequence element(s) in the amino acid sequence in question and the reference amino acid sequence that are likely to have the same structure and the (three-dimensional) alignment of these amino acid sequences.

Because protein structures are highly conserved, high levels of sequence similarity usually imply significant structural similarity (Marti-Renom, M. A., et al. (2000) Annu. Rev. Biophys. Biomol. Struct. 29: 291-325).

In one embodiment the homology model is generated by a method comprising the following steps:

reference structure selection, alignment of the sequence in question with the reference structure, model construction, and model assessment.

The alignment of the sequences can be performed using any alignment protocol, such as e.g. FASTA, BLAST, PSI-BLAST.

The homology model used in the methods of the current invention can be any homology model, such as a model obtained using the SWISS-model, CPHmodels, MODELER or LOOPER. In one embodiment the homology model is obtained by using the MODELER and LOOPER algorithms.

Homology models were built with an automated software script for the program MODELER 9v7 (83). Modeling templates were chosen based on sequence conservation from a reference structure database consisting of human, mouse, and chimeric antibody Fab fragment crystal structures with a minimum resolution of 2.8 Å, and without missing internal residues in their variable regions. The best resulting model for each monoclonal antibody was used as a basis for a loop refinement procedure (LOOPER, Discovery Studio, Accelrys Inc., San Diego, USA) (84). In turn, the five most likely solutions from loop refinement were selected and used as an ensemble of structures for each monoclonal antibody. Parameters were extracted computationally from these homology model ensembles (Table 2). The parameters "next different N-terminal secondary structure", "next different C-terminal secondary structure" and "position in coil" were deduced from the secondary structure information of surrounding residues using Boolean rules implemented in Pipeline Pilot (Accelrys Inc., San Diego, USA). The term "size of a C-terminal amino acid residue" denotes the solvent accessible surface area (SASA, 85) in Å$^2$ and is defined as follows: Ala, 64.78; Cys, 95.24; Asp, 110.21; Glu, 143.92; Phe, 186.7; Gly, 23.13; His, 146.45; Ile, 151.24; Lys, 177.37; Leu, 139.52; Met, 164.67; Asn, 113.19; Pro, 111.53; Gln, 147.86; Arg, 210.02; Ser, 81.22; Thr, 111.6; Val, 124.24; Trp, 229.62; Tyr, 200.31. A small C-terminal amino acid residue has a SASA of less than 111 Å$^2$. A big C-terminal amino acid residue has a SASA of 111 Å$^2$ or more.

The amino acid sequence of antibodies is given from the N-terminus to the C-terminus for each polypeptide chain. In the amino acid sequence each amino acid residue (except for the N-terminal amino acid residue) has a preceding amino acid residue. This preceding amino acid residue is located N-terminally to the amino acid residue in question. Also in the amino acid sequence each amino acid residue (except for the C-terminal amino acid residue) has a succeeding amino acid residue. This succeeding amino acid residue is located C-terminally to the amino acid residue in question. Therefore, the term "C-terminal amino acid residue" denotes the amino acid residue that is directly C-terminal to the Asn or Asp residue in question in the amino acid sequence, i.e. the amino acid residue that has an N-terminal amide bond to the respective Asn or Asp residue.

The term Fv-region denotes a pair of cognate antibody light chain variable domain and antibody heavy chain variable domain.

The term "change in carboxy-terminal secondary structure" denotes a change from a first secondary structure to a second different secondary structure. The term "secondary structure" denotes the secondary structures (alpha-)helix, (beta-)sheet, turn, and coil. Thus, a change in secondary structure is e.g. a change from helix to one of sheet, turn or coil, or from sheet to helix, turn or coil, or from coil to helix, sheet or turn.

Experimental Survey of Antibody Degradation Sites and Rates

A collection of 37 different therapeutic IgG1 and IgG4 monoclonal antibodies was investigated (Table 1).

TABLE 1

Experimental Asn and Asp hot-spot collection. Main modifications are written in bold. 15 out of 37 analyzed monoclonal antibodies contained at least one Asn/Asp hot-spot in one of the CDRs.

| monoclonal antibody | amino acid residue | modification | % modification | motif | location |
|---|---|---|---|---|---|
| mAb22 | Asp | iD + suc | 39 | DG | HC CDR3 |
| Omalizumab (11) | Asp | iD + suc | 31 | DG | LC CDR1 |

TABLE 1-continued

Experimental Asn and Asp hot-spot collection. Main modifications are written in bold. 15 out of 37 analyzed monoclonal antibodies contained at least one Asn/Asp hot-spot in one of the CDRs.

| monoclonal antibody | amino acid residue | modification | % modification | motif | location |
|---|---|---|---|---|---|
| mAb2 | Asp | iD + suc | 26 | DS | LC CDR2 |
| Trastuzumab (10, 49) | Asn | dea* + suc | 24 | NT | LC CDR1 |
| Trastuzumab (10, 49) | Asp | iD + suc | 22 | DG | HC CDR3 |
| mAb14 | Asn | dea | 22 | NS | LC CDR3 |
| mAb1‡ | Asn | dea + suc | 17 | NT | HC CDR3 |
| mAb22 | Asp | iD + suc | 12 | DG | LC CDR2 |
| mAbl 3 | Asp | iD + suc | 10 | DG | HC CDR3 |
| Nimotuzumab | Asp | iD + suc | 9 | DS | HC CDR3 |
| mAb26 | Asn | dea | 8 | NG | LC CDR1 |
| Nimotuzumab# | Asn | dea + suc | 8 | — | LC CDR1 |
| mAb32 | Asn | dea | 6 | NS | HC CDR2 |
| Infliximab | Asn | dea | 6 | NS | HC CDR2 |
| Natalizumab | Asn | dea + suc | 5 | NG | HC CDR2 |
| Trastuzumab (10, 49) | Asn | dea + suc | 5 | NG | HC CDR2 |
| mAb17 | Asn | dea + suc | 4 | NS | LC CDR1 |
| mAb14 | Asn | suc | 4 | NN | LC CDR1 |
| mAb11 | Asn | suc | 4 | NT | LC CDR1 |
| mAb20 | Asn | dea + suc | 3 | NG | HC CDR2 |
| mAb2 | Asp | iD + suc | 3 | DS | HC CDR3 | iD = isomerization,
suc = succinimide,
dea = deamidation
*only Asp as deamidation species
‡excluded from hot-spot data set because of interaction with a CDR glycosylation site which is not represented by the homology models
proof of modification site impossible with available methods (tryptic peptide, AspN peptide, CID fragmentation, HCD fragmentation)

These antibodies were subjected to controlled heat stress at a typical formulation pH of 6.0 at 40° C. for 2 weeks (stressed samples), and subsequently analyzed for degradation events by mass spectrometric analysis, which localized the affected residues and quantified the amount of modification in stressed and corresponding reference samples.

Out of all 559 Asn and Asp residues in the Fv regions of the 37 monoclonal antibodies, 60 residues (11%) exhibit quantifiable amounts of modification. These were sub-classified into 19 hot-spots, 13 weak-spots, and 28 reactive-spots. The term hot-spot corresponds to 3% or more, the term weak-spot to 1% up to less than 3%, and the term reactive-spot to less than 1% modification in the stressed samples.

Location of Degradation Sites

It has been found that degradation hot-spots with 3% or more modification are located in the CDR loops (see Table 1). Most hot-spots are located in the light chain CDR 1 and the heavy chain CDR 3, whereas heavy chain CDR 1 does not contain any hot-spot. 15 out of 37 analyzed monoclonal antibodies contain at least one Asn/Asp hot-spot in one of the CDRs. No hot-spots were observed in the Fv regions of monoclonal antibodies mAb3, mAb 4, mAb 9, mAb 10, mAb 12, mAb16, mAb18, mAb19, mAb21, mAb27, mAb28, mAb29, mAb31, mAb33, Bevacizumab, Cetuximab, Adalimumab, Denosumab, Efalizumab, Basiliximab, Pavilizumab, and Panitumab.

In one embodiment of all aspects as reported herein is the method for determining deamidation/isomerization/succinimide-formation (or Asn/Asp degradation) hot-spots in the light chain CDR 1 or/and the heavy chain CDR 3.

It was shown in previous studies that the amino acid residue succeeding Asn and Asp influences the rate of succinimide formation in proteins (40, 51). So far, eight different sequence motifs involved in chemical degradation within Fv regions of therapeutic antibodies have been described (Asn succeeded by Gly, Ser, or Thr, and Asp succeeded by Gly, Ser, Thr, Asp, or His) (10-14, 35, 46, 65-73). In accordance with previous observations, Asn-Gly and Asp-Gly motifs are by far most prone to modification, corresponding to 67% and 36% of hot-spots within CDR motifs, respectively (FIG. 2A and FIG. 2B).

Systematic Analysis of Degradation Site Structure

The structural environment of all Asn and Asp residues in the antibodies' Fv fragments (i.e. degrading and non-degrading) was characterized by a set of 20 parameters with a putative role in the degradation mechanism. Homology models of Fab fragments were generated by a state-of-the art homology modeling software and the resulting solutions from the program were evaluated on the basis of the modeling score. Parameters were extracted in silico from homology models by an automated procedure. Generally, the high homology to template structures results in precise homology models of framework and short CDR regions. However, modeling of long CDR loops is prone to large modeling uncertainties, partially due to the high inherent flexibility of such loops (74-77). Therefore, all CDRs were subjected to a loop modeling procedure, yielding a five-membered homology model ensemble. Like this, additional information on different possible CDR conformations was captured, without the necessity of demanding molecular dynamics simulations. The correlation between structural parameters and in vitro degradation was investigated by machine-learning algorithms. It has been found that the predicting model shows sufficient accuracy and low mis-prediction compared to conventional sequence motif-based methods.

As the discrimination of both Asn/Asp degradation hot-spots from stable Asn/Asp residues based on primary sequence only is prone to massive over-prediction (51), a set of 20 structural parameters has been identified to reflect the three dimensional environment of these amino acids. These parameters are described below. They were identified on the basis of their putative role in the degradation mechanism (see FIG. 1 and FIG. 3, Table 2) and were computationally extracted from the homology model ensembles.

TABLE 2

Parameters defining the two- and three-dimensional environment of Asn and Asp residues. Parameters that are drawn in FIG. 3 are marked with an asterisk.

| Parameter abbreviation | Parameter description | Parameter origin |
|---|---|---|
| Carbonyl/amino group leaving tendency | | |
| *H-bonds OD1/2 | Number of hydrogen bonds to the side chain oxygen atoms (distance cutoff 3.0 Å, angle cutoff 55°) | PyMOL python script |
| H-bonds ND2 | Number of hydrogen bonds to the side chain nitrogen atom (distance cutoff 3.0 Å, angle cutoff 55°) | PyMOL python script |
| $pK_a$ | $pK_a$ value of the Asp residue (PARSE forcefield) | pdb2pqr |
| Transition state accessibility | | |
| RMSD | Root mean square deviation for alpha-carbons of each residue in a set of models in Å | PyMOL python script |
| *SASA | Solvent-accessible surface area of all atoms of a residue in Å$^2$ | PyMOL python script |
| *$C_\gamma$—$N_{n+1}$ distance | Distance between the residue's $C_\gamma$ atom and the backbone nitrogen atom of the following residue in Å | PyMOL python script |

TABLE 2-continued

Parameters defining the two- and three-dimensional environment of Asn and Asp residues. Parameters that are drawn in FIG. 3 are marked with an asterisk.

| Parameter abbreviation | Parameter description | Parameter origin |
|---|---|---|
| *$C_\alpha$ distance$_{n-1-n+1}$ | Distance between the alpha-carbon of the preceding and the succeeding residue in Å | PyMOL python script |
| *phi | Backbone dihedral angle φ (C'—N—$C_\alpha$—C') | PyMOL python script |
| *psi | Backbone dihedral angle ψ (N—$C_\alpha$—C'—N) | PyMOL python script |
| $C_\gamma$—O—$N_{n+1}$—C' | Dihedral angle $C_\gamma$—O—$N_{n+1}$—C' | PyMOL python script |
| *chi 1 | Side chain dihedral angle χ1 | PyMOL python script |
| *successor size | Size of the succeeding residue in Å$^2$ | PP logic operation |
| $N_{n+1}$ nucleophilicity | | |
| *$N_{n+1}$ SASA | Solvent-accessible surface area of the backbone nitrogen atom of the following amino acid in Å$^2$ | PyMOL python script |
| *H-bonds $N_{n+1}$ | Number of hydrogen bonds to the backbone nitrogen atom of the following amino acid (distance cutoff 3.0 Å, angle cutoff 55°) | PyMOL python script |
| Structural environment | | |
| secondary structure | Secondary structure (sheet, helix, coil, turn) | Discovery studio script |
| *next different N-terminal secondary structure | The first residue within a different secondary structure in N-terminal direction (from −1 to −4; if <−4 then set to −20) | PP logic operation |
| *next different C-terminal secondary structure | The first residue within a different secondary structure in C-terminal direction (from 1 to 4; if >4 then set to 20) | PP logic operation |
| $F_{ab}$ location | Number that describes the position within the antibody $F_{ab}$ region. 1-14 corresponds to $F_v$ region | Java script |
| CDR loop | CDR loop number | PP logic operation |
| *position in coil | Position of a residue within a coil secondary structure (margin or center, otherwise not assigned) | PP logic operation |

A prerequisite for cyclic imide formation is the leaving tendency of the hydroxyl or the amino group of the Asp or Asn side chain, respectively. To estimate this tendency, the number of hydrogen bonds to the side chain oxygen atoms, or the side chain nitrogen atom was counted. For succinimide formation to occur, the carboxyl group of the Asp side chain must be protonated (33, 78). The probable protonation state was obtained by calculating the structure-dependent Asp pKa values using the established PROPKA algorithm (79). Accessibility and high nucleophilicity of the succeeding backbone nitrogen are other potential prerequisites for succinimide formation (see FIG. 1). Therefore, the succeeding backbone nitrogen's solvent accessible surface area was determined computationally and the number of hydrogen bonds was counted.

The transition state of the succinimide formation reaction requires the Asp or Asn head group to approach the backbone nitrogen of the succeeding residue. Transition state-like conformation was probed by measuring the distance of the side chain $C_\gamma$-atom to the $N_{n+1}$-atom (FIG. 1 and FIG. 3 (61)), the side chain dihedral angle $\chi 1$, and the dihedral angle CGONC that was defined as the angle between the atoms $C_\gamma$, O, $N_{n+1}$, and C. Additionally, the solvent-accessible surface area of each Asp or Asn was determined computationally. It was shown that the n+1 side chain influences the rate of succinimide formation (3, 5, 16, 29, 33, 51, 52, 54). Hence, the successor amino acid size is recorded, as well as the backbone dihedral angles $\phi$ ($C'_{n-1}$—N—$C_\alpha$—C') and $\psi$ (N—$C_\alpha$—C'—$N_{n+1}$) which provide essential three-dimensional information about the local structural conformation and thus the potential accessibility of the transition state.

Further parameters describe the broader structural environment. The root mean square deviation (RMSD) of the Asn/Asp residues' $C_\alpha$-atoms in the homology model ensemble reflects structural diversity within the ensemble and is seen as an indication of possible conformational flexibility. The secondary structure element (the residue is embedded in helix, sheet, turn, or coil) (34, 62), and the distance to the next different N- and C-terminal secondary structure element (51) are included as additional parameters. If a residue is located in a coil secondary structure, its position within the coil (margin or center) was annotated. To quantify the "bend" of a coil tip, the distance between the $C_\alpha$-atoms of the n−1 and the n+1 residue was measured. Finally, the location within the Fab fragment was attributed to each residue, namely in one of the CDRs, in the framework or in the CH1/CL domain.

Only residues in the antibodies' Fv part were used for classification because no CH1/CL hot-spots were observed. 2460 Asn and Asp residues (492 residues×5 models) derived from 185 homology models (37×5 models) were used for statistical analysis and include 95 hot-spots (19×5 models) with 3% or more modification in the stressed sample, as well as all 397 non-hot-spots. Training of the classifiers was performed with a random 75% training dataset (always keeping the 5-membered ensembles together), excluding terminal residues as well as weak-spots and reactive-spots to avoid misleading classification. Bayesian classification, recursive partitioning, support vector machines, random forests, regularized discriminant analyses, and neuronal networks were tested in 40 repeats of random training set assignments, using all 20 parameters (FIG. 4A, FIG. 4B, FIG. 5A and FIG. 5B).

improved classification scheme. A residue counts as a predicted hot-spot if at least one member of the five-membered ensemble was classified as such. To identify the best suited classifier out of the nine different classification models, a receiver operating characteristic (ROC) analysis, which is commonly applied to illustrate the performance of binary classification systems, was used. Therein, the fraction of true positives out of the positives (true positive rate, TPR) is plotted against the fraction of false positives out of the negatives (false positive rate, FPR). Weighting a high true-positive rate as the most important criterion, the Pipeline Pilot implementation of a single-tree lookahead-enabled recursive partitioning algorithm was chosen as the most suitable classifier (FIG. 4A, FIG. 4B, FIG. 5A and FIG. 5B). At each step, the recursive partitioning algorithm chooses a parameter that is the best in splitting the dataset into homogeneous subsets belonging to one class (hot-spot or non-hot-spot), whereas the splitting point is called a node, and the class is called a leaf. The integrated lookahead functionality ensures that the chosen splitting parameter and value is not only optimal for the given step but also for subsequent steps. Like this, the model identifies the most crucial parameters for distinguishing hot-spots from non-hot-spots. This classifier yields the best combination of a high TPR, a still acceptable FPR for prediction of Asn and Asp degradation propensity, and good algorithm interpretability, even after the following optimization procedure for prediction purposes.

The Asn and Asp single-tree lookahead-enabled recursive partitioning algorithms were optimized in order to enhance model performance for new data and to avoid over-fitting. Therefore, Asn and Asp trees were pruned, i.e. branches were systematically removed to yield smaller trees. To test the pruned models' predictivity, they were validated against a 25% test set in forty independent runs (FIG. 6A and FIG. 6B). Final Asn and Asp algorithms were trained with 100% of the data, and were chosen on the basis of the corresponding ROC plots (FIG. 6A and FIG. 6B) as well as meaningful tree interpretability. They are represented as decision trees in FIG. 7 and FIG. 8.

After forty runs of test set validation against the model trained with randomized 75% training sets, an average of 0.5 out of 8 Asp-hot-spots were not recognized, whereas an average of 6.6 out of 285 Asp non-hot-spots were assigned false-positively. This corresponds to a TPR of 0.94, being

TABLE 3

Average numbers of false-positive and false-negative Asn/Asp residues; TPR (true positive rate) = number of true positives divided by number of positives; FPR (false positive rate) = number of false positives divided by number of negatives.

| Asp Classifier | FPR | STDEV (FPR) | TPR | STDEV (TPR) | Asn Classifier | FPR | STDEV (FPR) | TPR | STDEV (TPR) |
|---|---|---|---|---|---|---|---|---|---|
| svm | 0.001 | 0.002 | 0.85 | 0.12 | svm | 0.001 | 0.003 | 0.85 | 0.10 |
| ksvm | 0.002 | 0.003 | 0.89 | 0.10 | ksvm | 0.005 | 0.005 | 0.86 | 0.10 |
| rpart | 0.010 | 0.008 | 0.84 | 0.13 | rpart | 0.033 | 0.018 | 0.78 | 0.14 |
| tree | 0.007 | 0.005 | 0.88 | 0.12 | tree | 0.012 | 0.007 | 0.86 | 0.11 |
| rda | 0.032 | 0.016 | 0.81 | 0.10 | rda | 0.015 | 0.014 | 0.73 | 0.21 |
| nnet | 0.068 | 0.041 | 0.94 | 0.08 | nnet | 0.188 | 0.129 | 0.90 | 0.08 |
| randomForest | 0.002 | 0.003 | 0.83 | 0.14 | randomForest | 0.006 | 0.006 | 0.87 | 0.10 |
| BayesClassifier | 0.018 | 0.006 | 0.90 | 0.11 | BayesClassifier | 0.035 | 0.015 | 0.84 | 0.11 |
| PP tree 4 | 0.023 | 0.010 | 0.94 | 0.10 | PP tree 4 | 0.043 | 0.025 | 0.95 | 0.08 |
| sequence based | 0.310 | — | 1.00 | — | sequence based | 0.410 | — | 1.00 | — |

Asn and Asp classifications were separately dealt with because Asn degradation could follow different mechanisms (5, 37-40), (FIG. 1). This separation finally led to an the number of true positives (7.5) divided by the number of positives (8), and a FPR of 0.02, defined as the number of false positives (6.6) divided by the number of negatives (285) (FIG. 4A). In the case of Asn, an average of 0.6 out of 11 Asn-hot-spots was assigned as false-negative (TPR=0.95) and 8.1 out 188 non-hot-spots were obtained as false-positives (FPR=0.04) (FIG. 4B). This is a significant improvement to prediction based on solely primary sequence information, which led to a strong over-prediction (Asp TPR=1.0, FPR=0.31; Asn TPR=0.91, FPR=0.43) (FIG. 4A and FIG. 4B).

Asp and Asn Degradation Propensity Depends on Residue Flexibility, Successor Size, and Secondary Structure In the case of Asp, the dataset consists of only 2.7% hot-spots that need to be distinguished from the non-hot-spot Asp residues. The first two decision tree splits can separate 93% of all non-hot-spots (1105, first split; 260, second split). Non-hot-spots are inflexible or are succeeded by a big carboxy-terminal amino acid, such as e.g. Pro, Thr, asn, Val, Leu, Glu, His, Gln, Ile, Met, Lys, Phe, Tyr, Arg or Trp. Thus, the remaining Asps to be classified are flexible and are succeeded by a small amino acid which could be Gly, Ala, Ser, Cys, or Asp. Of these, the first and biggest Asp hot-spot class is split off and is characterized by high conformational flexibility (RMSD>0.485 Å) and Asp, Cys, Ser, Ala or Gly as a successor. It contains 5 hot-spots (5 members each) as well as 2 false positive Asp residues (5 members each).

At the next node, hot-spot class 2 is split off. Its 3 members (1 with 5 homology model members, 1 with 2, and 1 with 1 member only) are characterized by moderate conformational flexibility (RMSD between 0.145 Å and 0.485 Å), can be followed by Asp, Cys, Ser, Ala or Gly, and a change in carboxy-terminal secondary structure within a stretch of less than 3 amino acids.

Hot-spot class 3 is characterized by an Asp residue within the Asp-Gly motif. Additionally, as class 2, it features moderate conformational flexibility (RMSD 0.145 Å-0.485 Å) and a change in carboxy-terminal secondary structure within more than 3 residues. It contains 2 hot-spots (1 with 4 homology model members, and 1 with 3 members) and 1 false-positive Asp (5 members).

Also for Asn degradation hot-spot classification, the main criteria are the size of the carboxy-terminal amino acid and conformational flexibility (FIG. 8). Compared to the Asp dataset, there are twice as many Asn hot-spots in relation to non-hot-spots, which correspond to 5.5%. Also here, the first two decision tree splits can separate the bulk of non-hot-spots (72%; 395, first split; 320, second split). Non-hot-spots are succeeded by a big carboxy-terminal amino acid (Val, Leu, Glu, His, Gln, Ile, Met, Lys, Phe, Tyr, Arg or Trp) or are inflexible (RMSD<0.01 Å). The next split criterion is the successor size and leads to 2 branches, containing Asn residues with a successor size less or greater than 102.7 Å2. The latter is further categorized by the CDR loop location. Thus, the first Asn hot-spot class contains residues in CDR loop 1, is further characterized by the carboxy-terminal residues Asp, Pro, Thr, or Asn, and is not inflexible (RMSD>0.01 Å). It contains 3 hot-spot members (5 homology model members each).

The residues with a successor size less than 102.7 Å$^2$ are further classified by their backbone dihedral angle phi. Asn residues followed by Gly, Ala, Ser, or Cys (<102.7 Å$^2$) that are not inflexible and whose phi angle is smaller than −75.2 degrees constitute the second and largest hot-spot class 2. It contains 6 hot-spot members (4 with 5 homology model members, 1 with 4, and 1 with 2 members), as well as 4 false-positives (1 with 5 homology model members, 2 with 3, and 1 with 1 member).

Hot-spot class 3 is defined by the same flexibility and successor characteristics as class 2 but its 4 members (2 with 5 homology model members, 1 with 3, and 1 with 1 member only) feature a phi angle greater than −75.2 degrees, high solvent exposure (SASA>89.4 Å$^2$) (calculated by e.g. PyMOL) and a change in amino-terminal secondary structure within a stretch of more than 3 amino acids. Two false-positive Asn residues (1 and 2 homology model members) are also part of this class.

SUMMARY

Spontaneous degradation of Asn and Asp residues in therapeutic proteins can occur during production, storage, and in vivo. In case of involvement in target binding, the formation of the degradation products succinimide, isoAsp, and Asp embedded in the CDRs can lead to reduction of target binding efficacy and a reduction of drug potency.

An in silico prediction tool was developed to facilitate selection of stable antibody candidates. To this end first a uniform data set that contains qualitative and quantitative data on antibody degradation products was derived. These detected modifications are in accordance with known hot-spot information.

At aspartyl residues, the side chain carboxyl group needs to be protonated for the degradation mechanism to occur as the hydroxyl group of the carboxylic acid is a better leaving group than the corresponding anion. Increasing pH promotes ionization of the backbone nitrogen atom of the succeeding residue rendering it more nucleophilic. When the pH reaches a value above 6, these opposing driving forces tend to offset each other and no pH dependency can be clearly seen (81).

Detection of relevant Asn degradation is most suitable at slightly acidic pH as elevation of the hydroxyl ion concentration leads to artificially high deamidation rates that do not allow to distinguish method-induced pH-artifacts from relevant degradation sites (49).

It has been found that no information from alkaline pH stability studies got lost under the slightly acidic conditions. Alkaline pH dependent hot-spots get modified in the course of fermentation (pH 7.4) and are characterized by similar degradation rates in reference and stress samples, thus by no significant increase after induced degradation at pH 6. Usually, a mixture of Asp and iso-Asp is obtained in variable ratios after succinimide hydrolysis (3, 53, 57). The occurrence of only one product, which was shown to be Asp, could possibly argue for a succinimide-independent degradation pathway—either via an alternative nucleophilic attack mechanism resulting in isoimide (37) or via direct Asn side chain hydrolysis (39). This phenomenon was observed at the Asn-Thr motif in Trastuzumab.

Strikingly, all observed hot-spots are located in the CDR loops of the antibodies tested (Table 1). Thus, the Fab fragment and the Fv framework represent a stable scaffold. To assess the relevance of our therapeutic monoclonal antibody collection in relation to naturally occurring antibodies, the frequency of the known Asn and Asp degradation sequence motifs (NG, NN, NS, NT, DG, DS, DT, DD, DH) was compared between the CDRs of our monoclonal antibody collection (combined Kabat and Chothia definitions (82)) and 16286 naturally occurring human monoclonal antibody sequences (9990 V-D-J and 6296 V-J sequences) from the international ImMunoGeneTics (IMGT) information system's® monoclonal antibody database (www.IMG-T.org). Despite the enormous difference in size of the compared datasets, the frequency at which Asn and Asp motifs occur, is distributed comparatively equally and shows that the sequence composition of the investigated antibody molecules is not biased (FIG. 2A and FIG. 2B). The only exception is the NT motif that is found twice as frequently in therapeutic monoclonal antibodies than in IMGT. Obviously, the most relevant motifs concerning degradation—Asn-Gly and Asp-Gly—do not occur frequently in both data sets compared to other sequence motifs.

As reported in the art, the prediction of Asn/Asp degradation propensity can be carried out based on primary sequence information and three dimensional structural information (5, 34, 37, 38, 40, 46, 51, 61-64). A tool for prediction of Asn deamidation in proteins was presented by Robinson & Robinson in 2001 (51). The authors used reported deamidation rates of 198 Asn residues in 23 different proteins and 70 Asn residues in 61 human hemoglobin variants that were observed under a wide variety of experimental conditions. The main differences to our study are that (i) the prediction is only applicable for Asn, (ii) the hot-spot collection—hence the basis for prediction—has no uniform experimental background, (iii) the three dimensional information stems from experimental X-ray structures, not from homology models, (iv) for general users the prediction is possible for proteins with entries in the PDB until 2001, and (v) it can be applied to new proteins only if X-ray information is available. In contrast to this method, the method as reported herein is adapted to the variable region of therapeutic antibodies, and is based on in silico calculations, bypassing the need for experimental X-ray structures. The prerequisites of the method as reported herein are (i) an antibody light and heavy chain amino acid sequence, (ii) a homology modeling tool, (iii) a molecular visualization software suite, and (iv) the statistical model as reported herein. The reduction of falsely assigned hot-spots (2.3% Asp, 4.3% Asn) compared to sequence-only based prediction (31% Asp, 43% Asn) is advantageous to save time and resources. The ratio of non-hot-spots to hot-spots was lowered by working with only the Fv part of the Fab fragment as only the variable region contained degradation-prone Asn and Asp. Classification with only residues embedded in the CDR loop led to less predictive statistical values.

Herein is reported a tool for predicting sites of antibody degradation and reveals the main characteristics that distinguish unstable and stable Asn and Asp amino acids in the variable region of monoclonal antibodies: Asn and Asp residues with high flexibility and a small successor are prone to degradation. They can be further characterized by secondary structural elements. It has surprisingly been found that parameters most promptly describing the reaction mechanism (FIG. 1) as the distance between the $C_\gamma$ atom and backbone nitrogen atom of the carboxy-terminal amino acid, the Asp $pK_a$ value, or the side-chain dihedral angle $\chi 1$, were not relevant for classification.

With the method as reported herein a more efficient pre-selection of monoclonal antibodies can be performed. In the process of finding the most stable, and at the same time most effective lead candidate molecule, which can be brought into further development and into the clinic, late stage failure can be circumvented and maximum benefit for the patient can be ensured.

The rule for a hot-spot alert is the following: if at least one Asn/Asp in a set of five homology models is predicted to be a hot-spot, the residue per se is classified as such. The probability for hot-spot classification can range from a 0.5 minimum to a 1.0 maximum for each member of the ensemble. Thus, prediction output is not only qualitative but also quantitative, expressed in the average of the probabilities of each member for being a hotspot including the standard deviation. Like this, the information if one, two, three, four, or five members of the ensemble are in hot-spot conformation, is contained in the prediction output.

DESCRIPTION OF THE FIGURES

FIG. 2A) Asn sequence motifs, FIG. 2B) Asp sequence motifs.

FIG. 4A) Aspartate validation, FIG. 4B) Asparagine validation.

Figure 1:
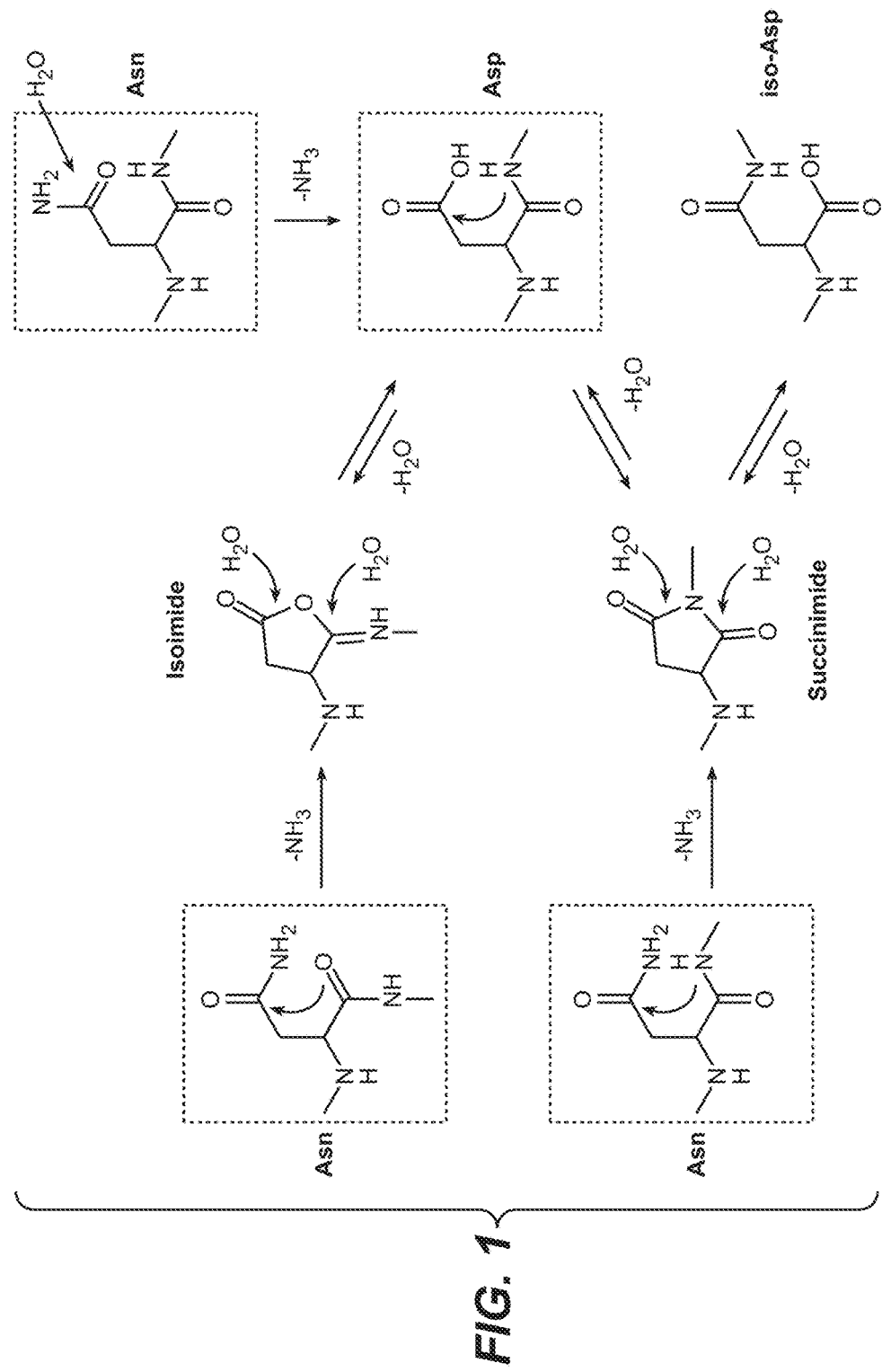
FIG. 1 Asparagine and Aspartate degradation pathways. Deamidation of asparagine or dehydration of aspartic acid occurs by nucleophilic attack of the α-amino group of the C-flanking amino acid. This leads to formation of a meta-stable succinimide (cyclic imide) intermediate, which hydrolyzes to a mixture of aspartyl and iso-aspartyl linkages. Alternatively, nucleophilic attack by the backbone carbonyl oxygen results in a cyclic isoimide intermediate, yielding only aspartyl residues after hydrolysis independent of the point of attack of the incoming water molecule. Asparagine residues can deamidated to Asp by direct water-assisted hydrolysis. Standard amino acids (Asn, Asp) are outlined by black boxes.
Figure 2A:
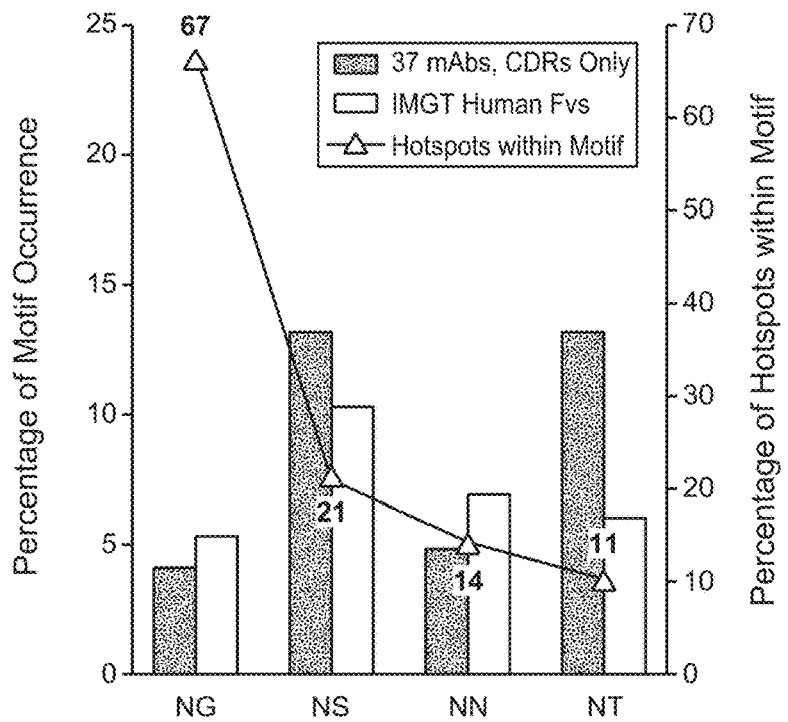
FIG. 2A and FIG. 2B Occurrence of Asn and Asp amino acid motifs in the CDRs of a therapeutic mAb collection and a set of naturally occurring antibodies (IMGT). Black triangles show percentages of hotspots within Asn and Asp motifs of the experimental collection of 37 mAbs. Bars represent percentages of depicted sequence motifs among all Asn or Asp residues in the variable region (upper panel) or only CDR regions (lower panel). Percentages shown as filled bars represent the non-redundant collection of the 37 analytically assessed therapeutic monoclonal antibodies, bars striped in light grey belong to a collection of 9990 V-D-J- and 6296 V-J regions of naturally occurring antibodies from the IMGT database.
Figure 2B:
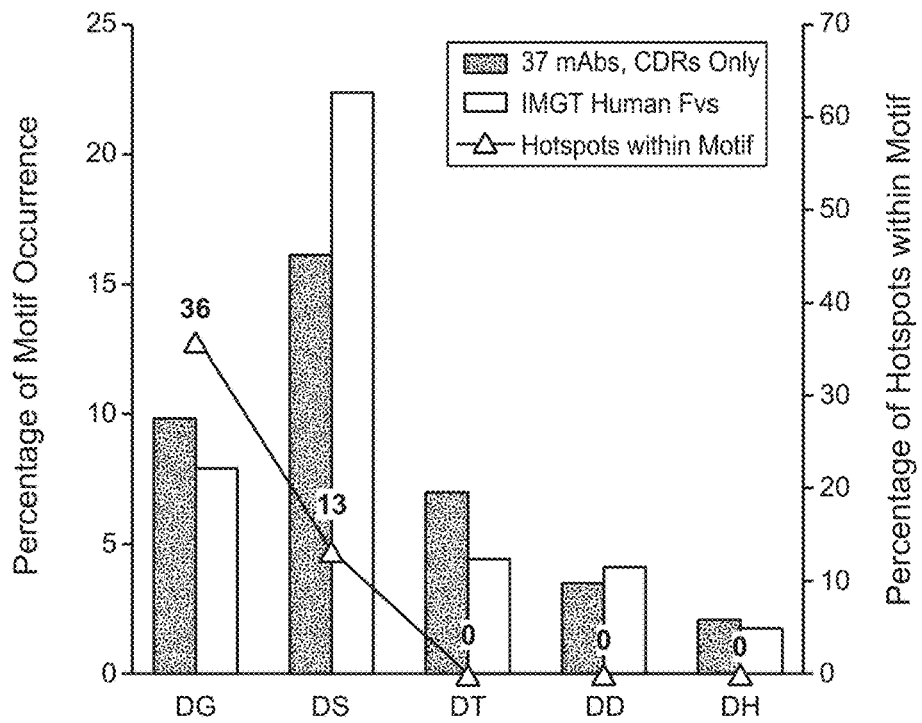
Figure 3:
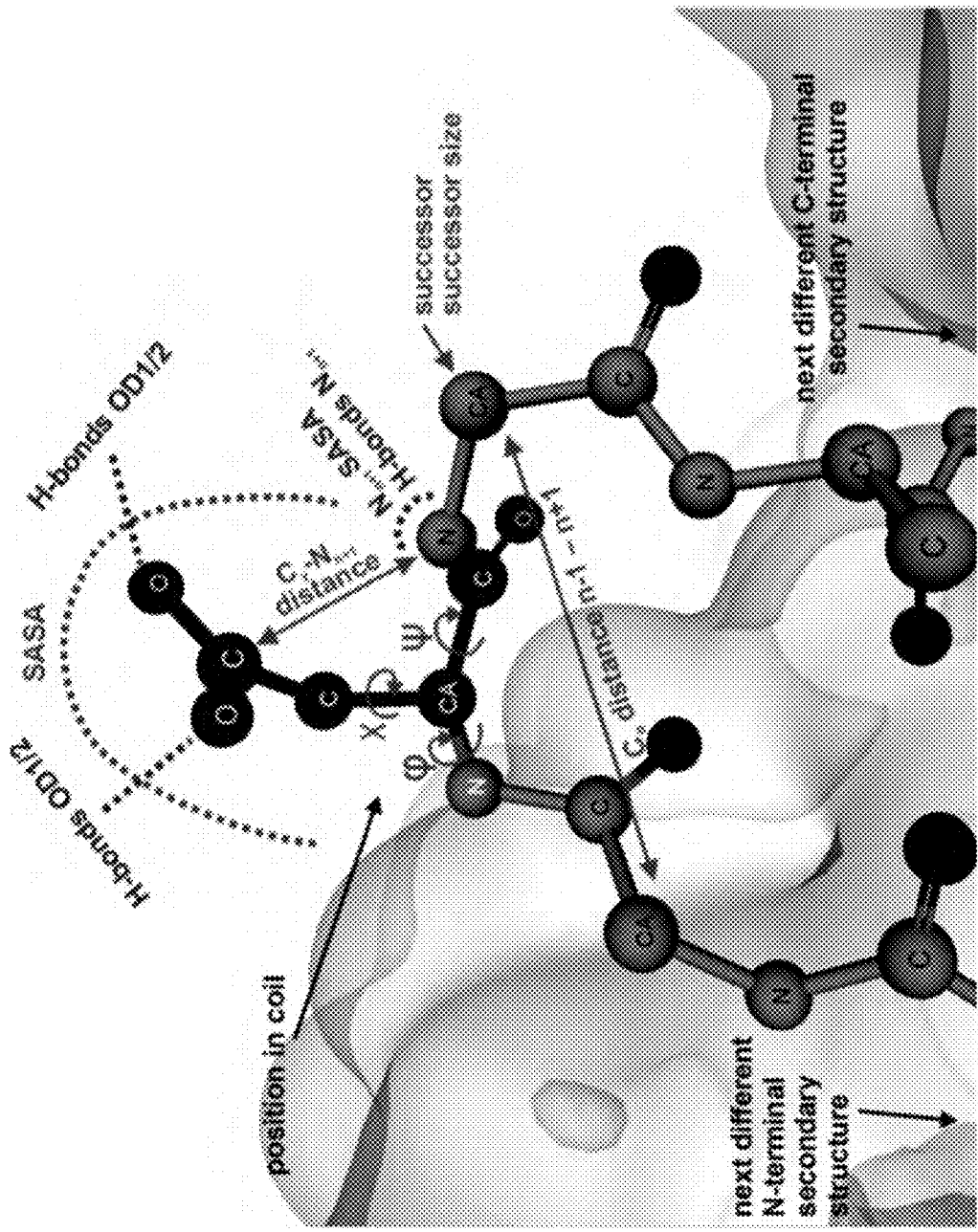
FIG. 3 Parameters characterizing Asn and Asp residues in a structural environment outlined at an exemplary Asp residue. Parameters describing the carboxyl/amino group leaving tendency, the transition state accessibility, the $N_{n+1}$ nucleophilicity, and the structural environment are depicted in pink, light blue, purple, and dark blue, respectively. Parameter names are used as in Table 2.
Figure 4A:
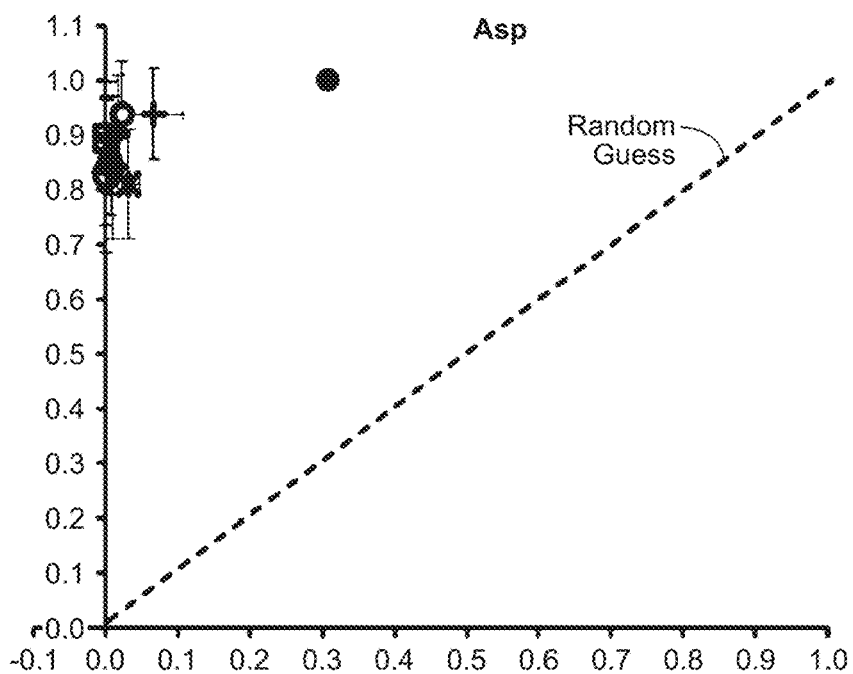
FIG. 4A and FIG. 4B ROC plot for comparison of three dimensional classifiers to sequence-based prediction shows significant decrease of false-positive rates. Evaluation of different statistical methods is compared with only sequence-based prediction. For statistical classification methods, average numbers of false-positive and false-negative Asn/Asp residues are results of 40 rounds of test set validation. TPR (true positive rate)=number of true positives divided by number of positives. FPR (false positive rate)=number of false positives divided by number of negatives. Tree (X), rpart (◊), PP (Pipeline Pilot) tree (shaded ○), and RandomForest (○) are recursive partitioning algorithms; svm (Δ), ksvm (□) are support vector machine algorithms; rda (✶) is a regularized discriminant analysis algorithm; nnet (+) is a neural network; sequence-based corresponds to prediction based on sequence motifs NG, NS, NT, and DG, DS, DT, DD, DH. The Pipeline Pilot tree, shown as a filled circle, was selected as prediction algorithm, at pruning level 4.
Figure 4B:
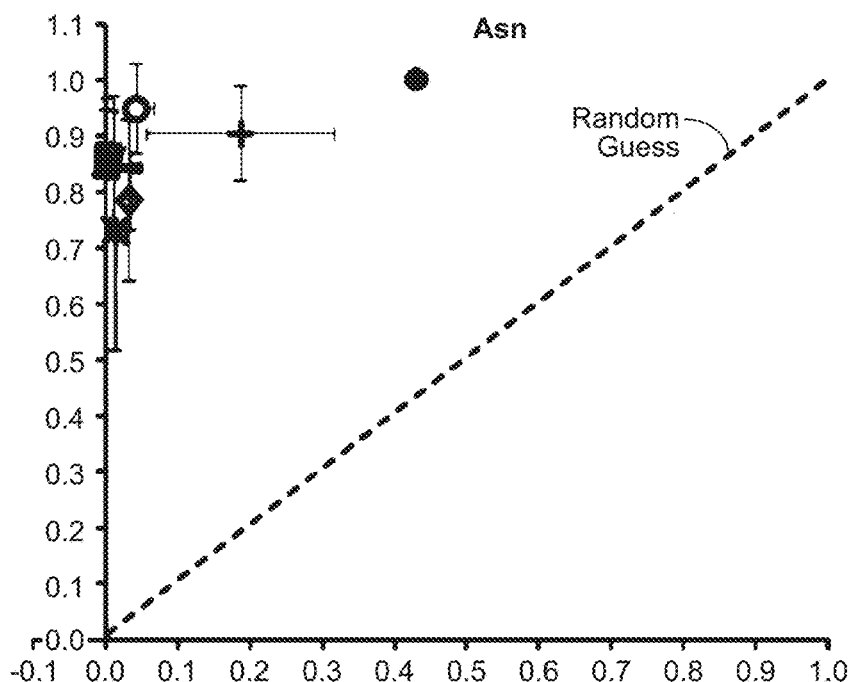
Figure 5A:
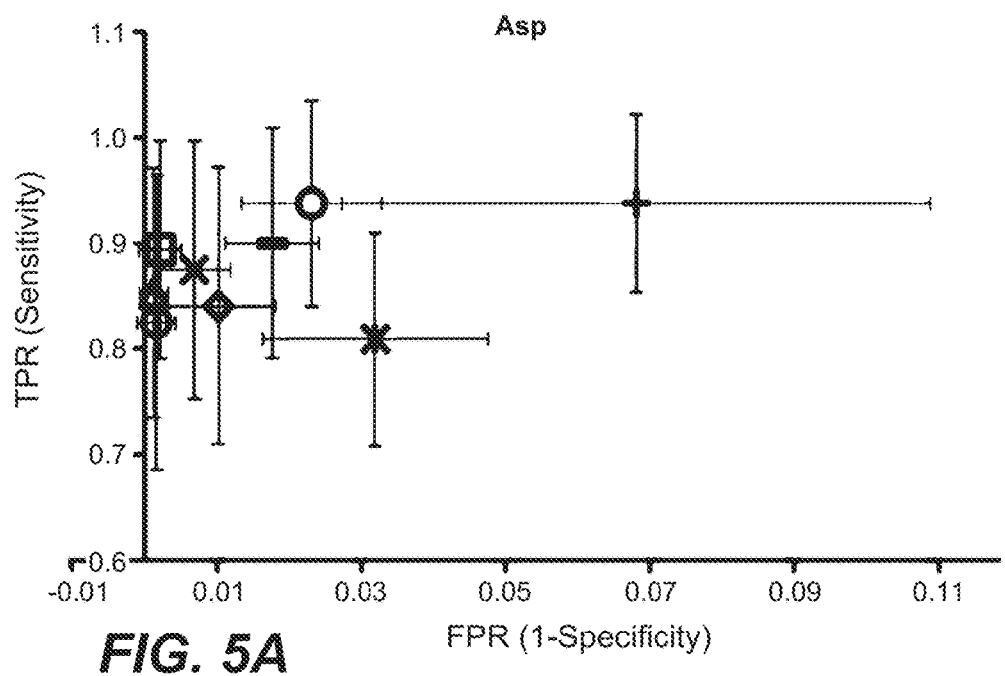
FIG. 5A and FIG. 5B Zoom into ROC plot (FIG. 4A and FIG. 4B) and table for comparison of three dimensional classifiers. Average numbers of false-positive and false-negative Asn/Asp residues are results of 40 rounds of test set validation. TPR (true positive rate)=number of true positives divided by number of positives. FPR (false positive rate)=number of false positives divided by number of negatives. Tree, rpart, PP (Pipeline Pilot) tree, and RandomForest are recursive partitioning algorithms; svm, ksvm are support vector machine algorithms; rda is a regularized discriminant analysis algorithm; nnet is a neural network. The Pipeline Pilot tree, shown as a shaded circle, was selected as prediction algorithm, at pruning level 4; a) aspartate validation, b) asparagine validation.
Figure 5B:
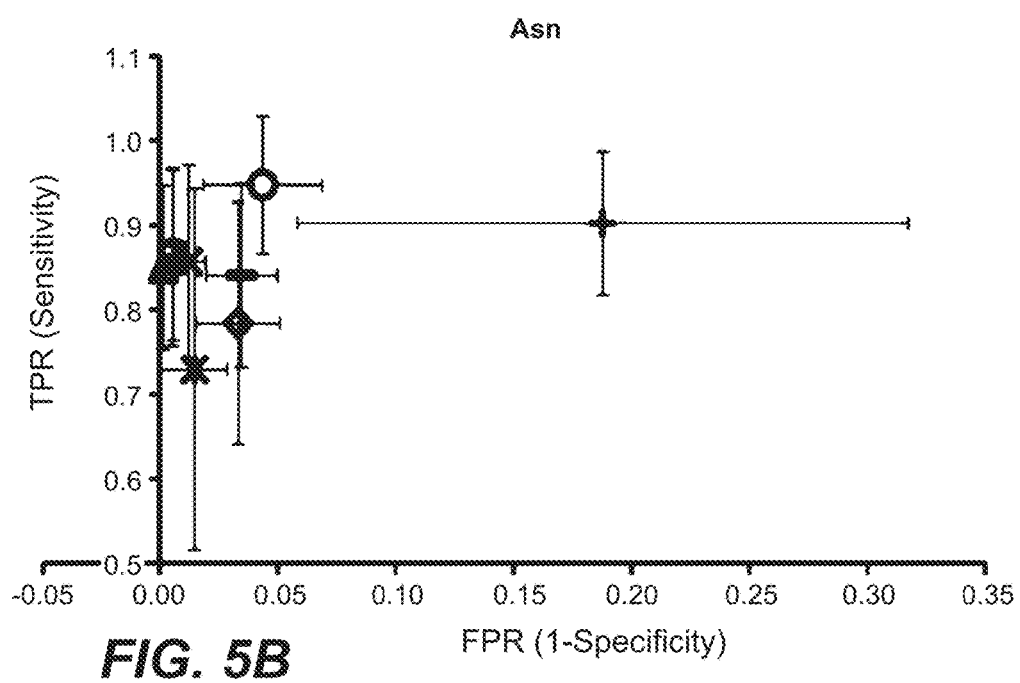
Figure 6A:
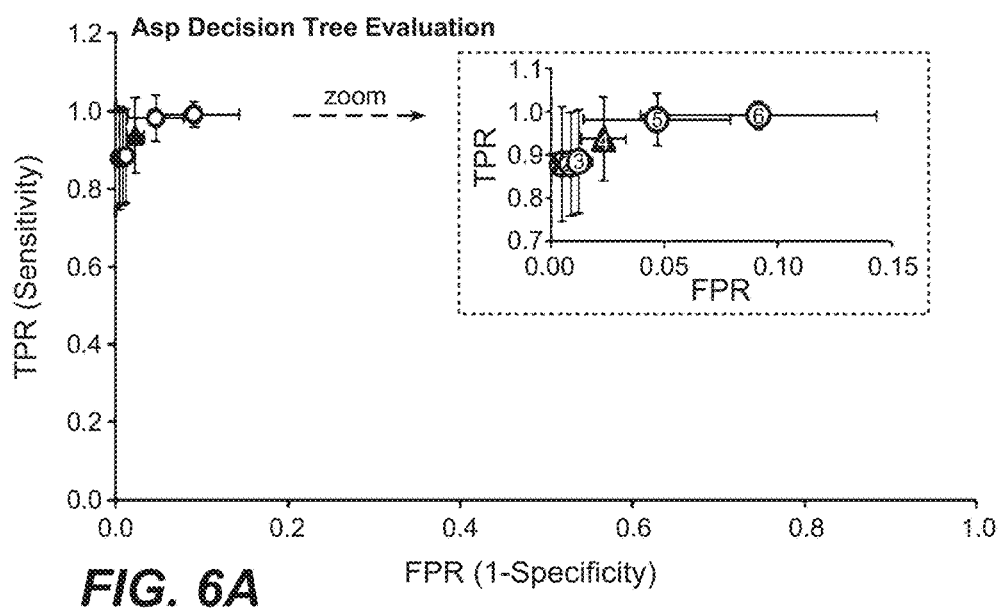
FIG. 6A and FIG. 6B ROC plot for comparison of different pruning levels of decision trees. Decision trees were pruned automatically as implemented in Pipeline Pilot (Accelrys Inc., San Diego, USA). Average numbers of false-positive and false-negative Asn/Asp residues are results of 40 rounds of test set (25%) validation. TPR (true positive rate)=number of true positives divided by number of positives. FPR (false positive rate)=number of false positives divided by number of negatives. Trees 1-3 and 5-6 are shown as spheres, tree 4 as a black triangle. Tree 1 is the un-pruned tree model. Tree 4 was selected for prediction. Overall, pruning level validation is based on the ROC plot, zoom areas show overlap of standard variations of different pruning levels.
Figure 6B:
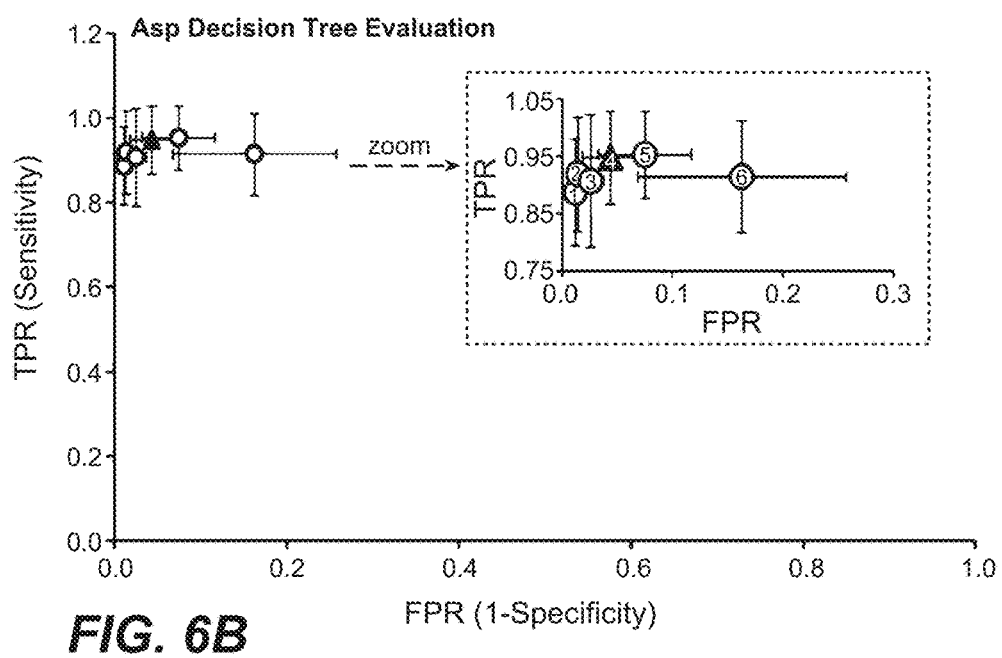
Figure 7:
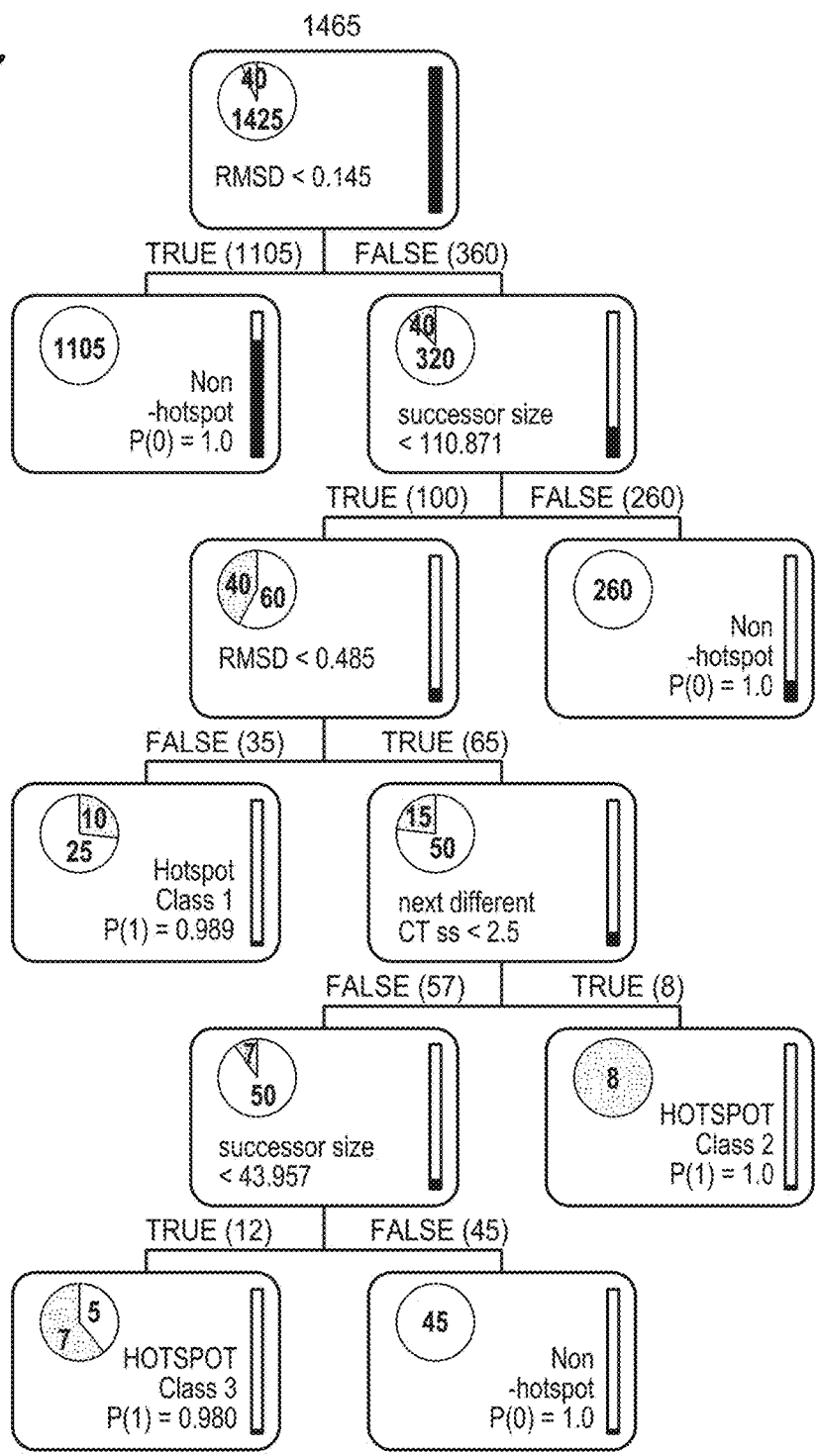
FIG. 7 Aspartate decision tree, pruning level 4, with look-ahead depth 4, and 7 look-ahead alternatives. The model was trained with 1425 non-hotspots (white) and 40 hotspots (black). The outline of nodes and leaves is colored by the weighted majority of the class that is present. Filling levels of the bars on the right hand side of each node/leaf refer to the fraction of the data set. The fraction of each class at a node/leaf is shown by the colored fraction of the circle. Main decision criteria are conformational flexibility (RMSD) and the size of the C-terminal amino acid (successor size); white=non-hot-spot; black=hot-spot.
Figure 8:
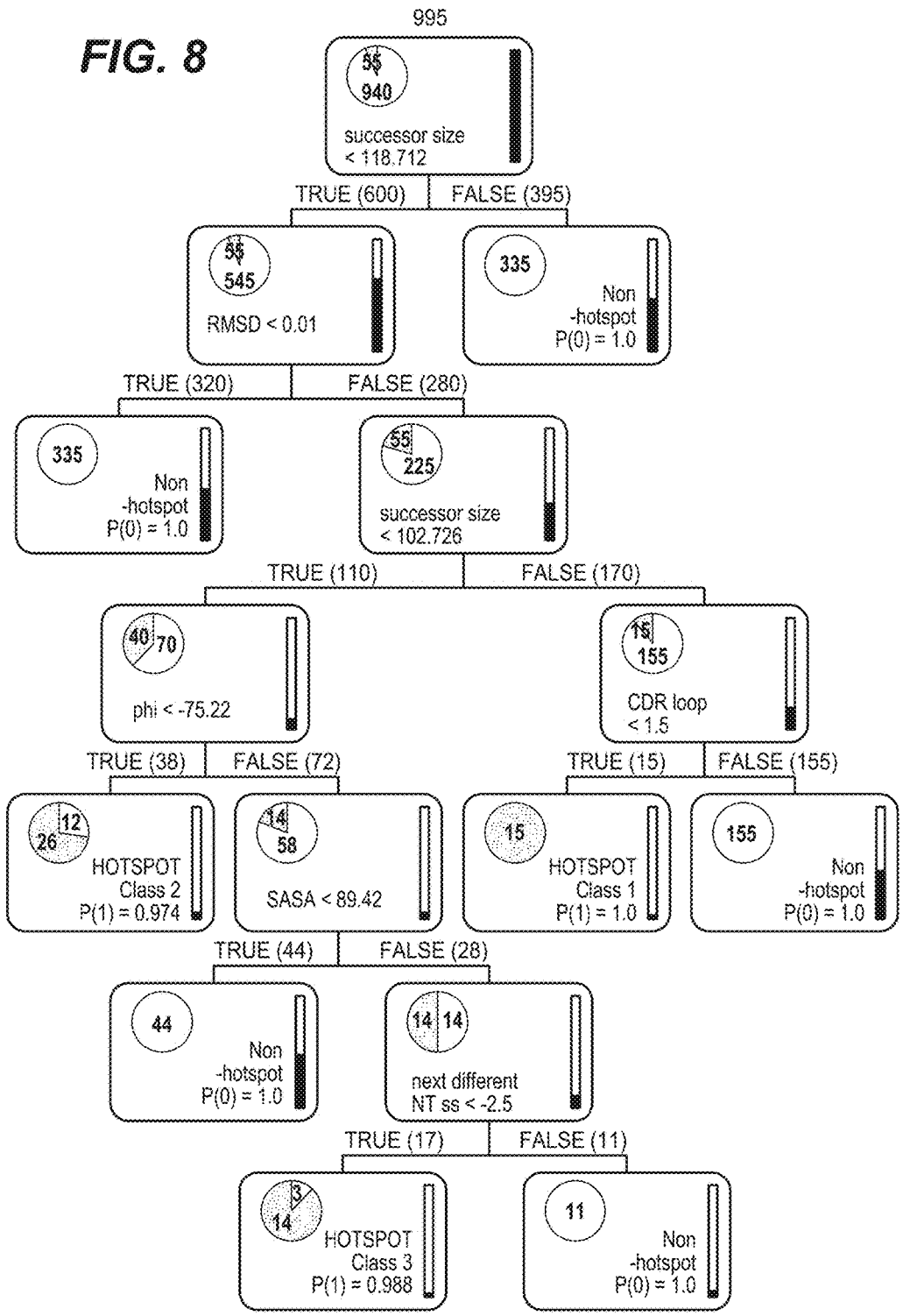
FIG. 8 Asparagine decision tree, pruning level 4, with look-ahead depth 4, and 7 look-ahead alternatives. The model was trained with 940 non-hot-spots (white) and 55 hot-spots (black). The outline of nodes and leaves are colored by the weighted majority of the class that is present. Filling levels of the bars on the right hand side of each node/leaf refer to the fraction of the data set. The fraction of each class at a node/leaf is shown by the colored fraction of the circle. Main decision criteria are the size of the succeeding amino acid and conformational flexibility (RMSD); white=non-hot-spot; black=hot-spot.

The examples and figures are provided to aid the understanding of the present invention, the true scope of which is set forth in the appended claims. It is understood that modifications can be made in the procedures set forth without departing from the spirit of the invention.

Materials and Methods

Monoclonal Antibody Origin

Twenty-four monoclonal antibodies are human or humanized IgG1 or IgG4 antibodies. Thirteen monoclonal antibodies are marketed products, including Avastin (Bevacizumab, Genentech/Roche); CYT387 (Nimotuzumab, Oncoscience, Ch.B.: 911017W002); Erbitux (Cetuximab, Bristol-Myers Squibb and Eli Lilly and Company, Lot: 7666001); Herceptin (Trastuzumab, RO-45-2317/000, Lot. HER401-4, Genentech); Humira (Adalimumab, Abbott, Ch.B.: 90054XD10); Prolia (Denosumab, Amgen, Ch.B.: 1021509); Raptiva (Efalizumab, Genentech, Merck Serono, Lot: Y11A6845); Remicade (Infliximab, Centocor, Ch.B.: ORMA66104); Simulect (Basiliximab, Novartis, Ch.B.: S0014); Synagis (Pavilizumab, Medimmune, Lot.: 122-389-12); Tysabri (Natalizumab, Biogen Idec and Elan, LotA: 080475); Vectibix (Panitumumab, Amgen, Ch.B.: 1023731); and Xolair (Omalizumab, Genentech/Novartis, Ch.B.: S0053).

Example 1

Generation of Samples with Induced Degradation

All therapeutic monoclonal antibodies were subjected to induced degradation (stressed samples). 2 mg of each antibody were dialyzed overnight at 4° C. into dilution buffer (20 mM histidine-chloride, pH 6.0) in D-Tube Dialyzers (Novagen, MWCO 6-8 kDa). Concentrations were determined (Nanodrop) and adjusted to 5 mg/ml with dilution buffer. After sterile filtration (Pall Nanosep MF, 0.2 µm) and transfer to sterile screw cap tubes, all monoclonal antibody samples were quiescently incubated for 2 weeks at 40° C.

Example 2

Monoclonal Antibody Sample Preparation for Tryptic Peptide Mapping Experiments

80 µg of monoclonal antibody reference and stressed sample were denatured and reduced for 1 hour in a final volume of 124.5 µL of 100 mM Tris, 5.6 M guanidinium hydrochloride, 10 mM TCEP (tris(2-carboxyethyl)phosphine, Pierce Protein Biology Products, Thermo Fisher Scientific, Waltham, Mass., USA), pH 6.0 at 37° C. Buffer was exchanged to 20 mM histidine chloride, 0.5 mM TCEP, pH 6.0 in 0.5 ml Zeba Spin Desalting Columns (Pierce Protein Biology Products, Thermo Fisher Scientific, Waltham, Mass., USA). Monoclonal antibodies were digested overnight at 37° C. by addition of 0.05 µg trypsin (Promega, Madison) per µg antibody in a final volume of 140 µL. Digestion was stopped by addition of 7 µL of 10% formic acid (FA) solution, and samples were frozen at −80° C. until further analysis.

Example 3

Detection of Modified Peptides by Liquid-Chromatography Tandem Mass-Spectrometry 14 µg of digested antibody was applied to an RP-HPLC (Agilent 1100 Cap LC, Agilent Technologies, Boeblingen, Germany) on a Varian Polaris 3 C18—Ether column (1×250 mm; 3 µm particle diameter, 180 Å pore size) from Varian (Darmstadt, Germany) for separation. The mAb2, mAb14, and Nimotuzumab digest were additionally separated by RP-UPLC (ACQUITY BEH300 C18 column, 1×150 mm, 1.7 µm bead size, 300 Å pore size, Waters, Manchester, UK). The HPLC or UPLC eluate was split using Triversa Nano-Mate (Advion, Ithaca, N.Y., USA) and 380 nL/min were infused into a LTQ Orbitrap classic tandem mass spectrometer (Thermo Fisher Scientific, Waltham, Mass., USA) operating in positive ion mode. The mobile phases of RP-HPLC consisted of 0.1% formic acid in water (solvent A) and 0.1% formic acid in acetonitrile (solvent B). The HPLC was carried out using a stepwise gradient starting at 2% solvent B, elevated to 15% from minute 5 to minute 15, to 32% from minute 15 to minute 70, to 38% from minute 70 to minute 80, to 100% from minute 80 to minute 90, and finally dropped to 2% from minute 92 to minute 110 with a flow rate of 60 µL/min. UPLC was effected with a linear gradient from 1 to 40% solvent B from 0 to 130 min. UV absorption was measured at wavelengths of 220 and 280 nm. Data acquisition was controlled by Xcalibur™ software (Thermo Fisher Scientific, Waltham, Mass., USA). For MS/MS measurements, fragmentation was induced by low-energy CID using helium as a collision gas with 35% collision energy in the LTQ. To obtain higher resolution of the fragment ions for mAb 14 and Nimotuzumab, the fragmentation was performed in the Orbitrap using a parent mass list, an isolation width of 3, a parent mass width of 0.2 Da, AGC Target 400000, and acquisition time of 5000 ms.

Example 4 mAb14 and Nimotuzumab Sample Preparation for MS/MS Evaluation

For further characterization, mAb14 and Nimotuzumab stressed samples were treated as follows. 250 µg of the monoclonal antibody was denatured by addition of denaturing buffer (0.4 M Tris (Sigma-Aldrich, Taufkirchen, Germany), 8 M guanidinium hydrochloride (Sigma-Aldrich, Taufkirchen, Germany), pH 8) to a final volume of 240 µL. Reduction was achieved by addition of 20 µL of 0.24 M dithiothreitol (DTT) (Roche Diagnostics GmbH, Mannheim, Germany) freshly prepared in denaturing buffer and incubation at 37° C. for 60 min. Subsequently, the sample was alkylated by addition of 20 µL of 0.6 M iodoacetic acid (Merck KgaA, Darmstadt, Germany) in water for 15 min. at room temperature in the dark. The excess of alkylation reagent was inactivated by addition of 30 µL of DTT solution. The samples were then buffer exchanged to approximately 480 µL of 50 mM Tris/HCl, pH 7.5 using NAPS Sephadex G-25 DNA grade columns (GE Healthcare, Germany). The monoclonal antibodies were digested 5 hours at 37° C. by addition of 0.03 µg trypsin (Promega, Madison) per µg protein in a final volume of 500 µL. Digestion was stopped by addition of 20 µL of 10% formic acid solution, and samples were frozen at −80° C. until further analysis.

Example 5

Data Analysis for the Quantification of Modification Levels

SIEVE software version 2.0 (VAST Scientific Inc., Cambridge, Mass.) was used to pre-filter data for differences between stressed and reference samples. Crucial SIEVE settings were a frame time width of 1.0 min, m/z width of 8.0 ppm, and an intensity threshold of 50,000 counts. SIEVE data filtered for monoisotopic masses (prelement=0) was imported into a macro-enabled EXCEL workbook as well as data from in silico tryptic digestion of monoclonal antibodies' heavy and light chains, containing theoretical mass-to-charge ratios of modified and unmodified peptides. Differences in signal intensities or retention time (reference vs. stress) of relevant m/z values of peptides were detected in a semi-automatized fashion by a macro-enabled EXCEL workbook (Microsoft, Redmond, Wash., USA). The resulting pre-filtered peptides from 76 peptide maps were manually inspected to verify Asn and Asp modifications by their m/z-values within the experimental mass spectrum. For quantification, extracted ion chromatograms (XICs) of peptides of interest were generated on the basis of their monoisotopic mass and detected charge states using Xcalibur Software (Thermo Fisher Scientific, Waltham, Mass., USA). Relative amounts of modified vs. unmodified peptides were calculated after manual integration of the corresponding peak areas. Additionally, all peptides lying in the CDR regions containing a putative hotspot motif (Asn-Gly, Asn-Thr, Asn-Ser, Asn-Asn, Asp-Gly, Asp-Thr, Asp-Ser, Asp-Asp, Asp-His) were analyzed even if not alerted after SIEVE software analysis to ensure completeness of the data.

Example 6

Homology Modeling and Extraction of Two- and Three-Dimensional Parameters

Homology models were built with an automated software script for the program MODELER 9v7 (83). Modeling templates were chosen based on sequence conservation from a reference structure database consisting of human, mouse, and chimeric antibody Fab fragment crystal structures with a minimum resolution of 2.8 Å, and without missing internal residues in their variable regions. The best resulting model for each monoclonal antibody was used as a basis for a loop refinement procedure (LOOPER, Discovery Studio, Accelrys Inc., San Diego, USA) (84). In turn, the five most likely solutions from loop refinement were selected and used as an ensemble of structures for each monoclonal antibody. Parameters were extracted computationally from these homology model ensembles (Table 2). The $pK_a$ value was calculated using the program propka as part of pdb2pqr (79). The secondary structure elements (sheet, helix, turn, coil) were extracted with a custom script using Discovery Studio (Accelrys Inc., San Diego, USA). The parameters "next different N-terminal secondary structure", "next different C-terminal secondary structure" and "position in coil" were deduced from the secondary structure information of surrounding residues using Boolean rules (Table 2) implemented in Pipeline Pilot (Accelrys Inc., San Diego, USA). A "margin" "position in coil" is assigned if the next different secondary structure element is one or two residues away, either in N- or C-terminal direction. A "center" "position in coil" is assigned if in both N- and C-terminal direction the secondary structure is the same for 4 residues or in both directions for more than 4 residues. The parameter "Fab location" is a number that was deduced from combined Chothia and Kabat CDR definitions for antibodies (82) (Kabat). "Fab location" number 1 corresponds to framework 1 of the heavy chain (FR H), 2 to CDR H 1, 3 to FR H 2, 4 to CDR H 2, 5 to FR H 3, 6 to CDR H 3, 7 to FR H 4, 8 to framework 1 of the light chain (FR L), 9 to CDR L 1, 10 to FR L 2, 11 to CDR L 2, 12 to FR L 3, 13 to CDR L 3, and 14 to FR L 4. "CDR loop" is a number ranging from 1 to 3, equal for light and heavy chain. "Successor size" is the solvent accessible surface area (85) in $Å^2$ and is defined as follows: Ala, 64.78; Cys, 95.24; Asp, 110.21; Glu, 143.92; Phe, 186.7; Gly, 23.13; His, 146.45; Ile, 151.24; Lys, 177.37; Leu, 139.52; Met, 164.67; Asn, 113.19; Pro, 111.53; Gln, 147.86; Arg, 210.02; Ser, 81.22; Thr, 111.6; Val, 124.24; Trp, 229.62; Tyr, 200.31. Terminal residues (lacking phi and psi) are marked in our data collection. All other parameters were extracted from the PDB files with self-written python scripts in PyMOL (5) (Table 2).

Example 7

Machine Learning Algorithms Used for Classification Assessment

In order to find the best possible classifier, several different methods, that were most suitable for this type of classification problem, were tested, namely support vector machines, recursive partitioning algorithms, regularized discriminant analysis and neuronal networks. They were available as packages for the statistical software R or in Pipeline Pilot (Accelrys Inc., San Diego, USA). Support vector machines (SVM) offer different ways to transform a given data set into higher dimensions with the help of a so called kernel function. Here, the svm method (86) from the package e1071 and the ksvm method from the kernlab package (87) were used. Recursive partitioning methods identify parameters in a step-wise manner to split the given data set into subsets, thereby producing a decision tree. The difference between the algorithms is mainly due to different methods to decide on the best splitting parameter in a given step. The "tree" (88) and "rpart" (89) methods were used in R whereby several different splitting methods were tested. A more generalized form of classifier can be achieved by combining decision trees based upon subsets of the original training set into a so-called random forest. Regularized discriminant analysis builds a classifier by combining a subset of the available parameters using regularized group covariance matrices in order to achieve best possible discrimination. This method is implemented as the function "rda" in the klaR package (90). A neural network tries to emulate the basic functionality of one or several interconnected layers of neurons. A so-called single-hidden-layer neural network as implemented in the "nnet" method of R (91) was applied. Finally, a naïve Bayes classifier, a probabilistic method that uses Bayes' theorem to compute probabilities of a data sample belonging to a certain class, given the training data, was tested as implemented in the "Naive-Bayes" method of R.

As a highly imbalanced dataset with very few hotspots but many non-hotspots had to be dealt with, class weights were introduced to put more emphasis on the minority class. A standard weighting scheme was identified, using the inverse of the class frequency, as the best in terms of classification error with special emphasis on the false negative rate.

Example 8

Recursive Partitioning and Prediction

After comparative evaluation of the methods in Example 7, the best-performing classification algorithm was a single-tree lookahead-enabled recursive partitioning algorithm in Pipeline Pilot (Accelrys Inc., San Diego, USA). The model was trained separately for Asn and Asp prediction with residues only from the homology models' Fv region. Thus, training was accomplished with 1045 Asn and 1520 Asp residues, 60 and 35 of which were hotspots, respectively, and the learned property was defined as hotspot. Terminal residues as well as residues with less than 3% modification rate in the stressed sample (weak spots and reactive spots) were excluded from the training. All 20 parameters described were supplied to the training set. A main feature of the single-tree recursive partitioning classification algorithm in Pipeline Pilot is the opportunity to assign a certain "look-ahead" depth that allows for better classification due to testing more alternative splits.

The two resulting prediction models are applied to new data. The rule for a hot-spot alert is the following: if at least one Asn/Asp in a set of five homology models is predicted to be a hot-spot, the residue per se is classified as such. The probability for hot-spot classification can range from a 0.5 minimum to a 1.0 maximum for each member of the ensemble. Thus, prediction output is not only qualitative but also quantitative, expressed in the average of the probabilities of each member for being a hot-spot including the standard deviation. Like this, the information if one, two, three, four, or five members of the ensemble are in hot-spot conformation, is contained in the prediction output.

REFERENCE LIST (1) Reichert, J. M., et al. (2005) Nat. Biotechnol. 23, 1073-1078.
(2) Swann, P. G., et al. (2008) Curr. Opin. Immunol. 20, 493-499.
(3) Geiger, T. & Clarke, S. (1987) J. Biol. Chem. 262, 785-794.
(4) Joshi, A. B., et al. (2005) J. Pharm. Sci. 94, 1912-1927.
(5) Clarke, S. (1987) Int. J. Pept. Protein Res. 30, 808-821.
(6) Manning, M. C., et al. (1989) Pharm. Res. 6, 903-918.
(7) Wakankar, A. A. & Borchardt, R. T. (2006) J. Pharm. Sci. 95, 2321-2336.
(8) Simpson, R. J. (2010) Cold Spring Harb. Protoc. 2010.
(9) Wakankar, A. A., et al. (2007) J. Pharm. Sci. 96, 1708-1718.
(10) Harris, R. J., et al. (2001) J. Chromatogr. B Biomed. Sci. Appl. 752, 233-245.
(11) Cacia, J., et al. (1996) Biochemistry 35, 1897-1903.
(12) Huang, L., et al. (2005) Anal. Chem. 77, 1432-1439.
(13) Yan, B., et al. (2009) J. Pharm. Sci. 98, 3509-3521.
(14) Rehder, D. S., et al. (2008) Biochemistry 47, 2518-2530.
(15) Weintraub, S. J. & Manson, S. R. (2004) Mech. Ageing Dev. 125, 255-257.
(16) Robinson, N. E. & Robinson, A. B. (2001) Proc. Natl. Acad. Sci. USA 98, 944-949.
(17) Robinson, N. E. & Robinson, A. B. (2001) Proc. Natl. Acad. Sci. USA 98, 12409-12413.
(18) Robinson, N. E. (2002) Proc. Natl. Acad. Sci. U.S.A 99, 5283-5288.
(19) Robinson, A. B., et al. (1970) Proc. Natl. Acad. Sci. U.S.A 66, 753-757.
(20) Wright, H. T. (1991) Crit. Rev. Biochem. Mol. Biol. 26, 1-52.
(21) Harding, J. J., et al. (1989) Mech. Ageing Dev. 50, 7-16.
(22) Zhao, R., et al. (2004) Cancer Cell 5, 37-49.
(23) Zhao, R., et al. (2007) PLoS. Biol. 5, el. doi.10.1371.
(24) Deverman, B. E., et al. (2002) Cell 111, 51-62.
(25) Weintraub, S. J. & Deverman, B. E. (2007) Sci. STKE. 2007.
(26) Takata, T., et al. (2008) Protein Sci. 17, 1565-1575.
(27) Takata, T., et al. (2007) Biochemistry 46, 8861-8871.
(28) Kosugi, S., et al. (2008) Biochem. Biophys. Res. Commun. 371, 22-27.
(29) Tomizawa, H., et al. (1994) Biochemistry 33, 8770-8774.
(30) Shimizu, T., et al. (2005) Biol. Pharm. Bull. 28, 1590-1596.
(31) Bohme, L., et al. (2008) Biol. Chem. 389, 1055-1066.
(32) Bohme, L., et al. (2008) Biol. Chem. 389, 1043-1053.
(33) Stephenson, R. C. & Clarke, S. (1989) J. Biol. Chem. 264, 6164-6170.
(34) Xie, M., et al. (2000) J. Pept. Res. 56, 165-171.
(35) Chu, G. C., et al. (2007) Pharm. Res. 24, 1145-1156.
(36) Oliyai, C. & Borchardt, R. T. (1993) Pharm. Res. 10, 95-102.
(37) Athmer, L., et al. (2002) J. Biol. Chem. 277, 30502-30507.
(38) Sinha, S., et al. (2009) Protein Sci. 18, 1573-1584.
(39) Catak, S., et al. (2009) J. Phys. Chem. A 113, 1111-1120.
(40) Wright, H. T. (1991) Protein Eng. 4, 283-294.
(41) Vlasak, J. & Ionescu, R. (2008) Curr. Pharm. Biotechnol. 9, 468-481.
(42) Zhang, W. & Czupryn, M. J. (2003) J. Pharm. Biomed. Anal. 30, 1479-1490.
(43) Kroon, D. J., et al. (1992) Pharm. Res. 9, 1386-1393.
(44) Zabrouskov, V., et al. (2006) Biochemistry 45, 987-992.
(45) Liu, H., et al. (2008) J. Chromatogr. A 1210, 76-83.
(46) Sreedhara, A., et al. (2012) Pharm. Res. 29, 187-197.
(47) Chelius, D., et al. (2005) Anal. Chem. 77, 6004-6011.
(48) Liu, H., et al. (2006) J. Chromatogr. B Analyt. Technol. Biomed. Life Sci. 837, 35-43.
(49) Diepold, K., et al. (2012) PLoS. One. 7, e30295. doi: 10.1371.
(50) Yu, X. C., et al. (2011) Anal. Chem. 83, 5912-5919.

(51) Robinson, N. E. & Robinson, A. B. (2001) Proc. Natl. Acad. Sci. USA 98, 4367-4372.
(52) Brennan, T. V. & Clarke, S. (1995) Int. J. Pept. Protein Res. 45, 547-553.
(53) Tyler-Cross, R. & Schirch, V. (1991) J. Biol. Chem. 266, 22549-22556.
(54) Oliyai, C. & Borchardt, R. T. (1994) Pharm. Res. 11, 751-758.
(55) Kosky, A. A., et al. (2009) Pharm. Res. 26, 2417-2428.
(56) Capasso, S. (2000) J. Pept. Res. 55, 224-229.
(57) Patel, K. & Borchardt, R. T. (1990) Pharm. Res. 7, 703-711.
(58) Oliyai, C., et al. (1994) Pharm. Res. 11, 901-908.
(59) Brennan, T. V. & Clarke, S. (1993) Protein Sci. 2, 331-338.
(60) Zheng, J. Y. & Janis, L. J. (2006) Int. J. Pharm. 308, 46-51.
(61) Kossiakoff, A. A. (1988) Science 240, 191-194.
(62) Xie, M. & Schowen, R. L. (1999) J. Pharm. Sci. 88, 8-13.
(63) Kosky, A. A., et al. (1999) Protein Sci. 8, 2519-2523.
(64) Bischoff, R. & Kolbe, H. V. (1994) J. Chromatogr. B Biomed. Appl. 662, 261-278.
(65) Wakankar, A. A., et al. (2007) Biochemistry 46, 1534-1544.
(66) Yi, L., et al. (2012) J. Pharm. Sci. 102, 947-959.
(67) Zhang, J., et al. (2011) Anal. Biochem. 410, 234-243.
(68) Xiao, G., et al. (2007) Anal. Chem. 79, 2714-2721.
(69) Timm, V., et al. (2010) J. Chromatogr. B Analyt. Technol. Biomed. Life Sci. 878, 777-784.
(70) Perkins, M., et al. (2000) Pharm. Res. 17, 1110-1117.
(71) Vlasak, J., et al. (2009) Anal. Biochem. 392, 145-154.
(72) Xiao, G. & Bondarenko, P. V. (2008) J. Pharm. Biomed. Anal. 47, 23-30.
(73) Valliere-Douglass, J., et al. (2008) Anal. Chem. 80, 3168-3174.
(74) Al-Lazikani, B., et al. (1997) J. Mol. Biol. 273, 927-948.
(75) Morea, V., et al. (1998) J. Mol. Biol. 275, 269-294.
(76) Martin, A. C. & Thornton, J. M. (1996) J. Mol. Biol. 263, 800-815.
(77) Whitelegg, N. & Rees, A. R. (2004) Methods Mol. Biol. 248, 51-91.
(78) Capasso, S., et al. (1992) Pept. Res. 5, 325-330.
(79) Li, H., et al. (2005) Proteins 61, 704-721.
(80) Hambly, D. M., et al. (2009) Anal. Chem. 81, 7454-7459.
(81) Zhigiang, A. (2009) in Therapeutic monoclonal antibodies: from bench to clinic. (Wiley & Sons, Inc., Hoboken, N.J.).
(82) Chothia, C., et al. (1989) Nature 342, 877-883.
(83) Sali, A. & Blundell, T. L. (1993) J. Mol. Biol. 234, 779-815.
(84) Spassov, V. Z., et al. (2008) Protein Eng. Des. Sel. 21, 91-100.
(85) Chennamsetty, N., et al. (2009) Proc. Natl. Acad. Sci. USA 106, 11937-11942.
(86) Dimitriadou, E., et al. (2011), http://CRAN.R-project.org/package=e1071.
(87) Karatzoglou, A., et al. (2004) Journal of Statistical Software 11, 1-20.
(88) Ripley, B. (2011) http://CRAN.R-project.org/package=tree).
(89) Therneau, R. M., et al. (2010) http://CRAN.R-project.org/package=rpart).
(90) Weihs, C., et al. (2005) in Data Analysis and Decision, eds. Baier, D., Decker, R., & Schmidt-Thieme, L. (Springer-Verlag, Berlin), pp. 335-343.
(91) Venables, W. N. & Ripley, B. D. (2002) Modern Applied Statistics with S. (Springer, New York.)

The invention claimed is:

1. A method for selecting one or more antibodies with degradation stability of Asp and Asn residues, the method comprising the following steps
   a) providing two or more antibodies,
   b) determining for each Asp and Asn residue in an antibody Fv region the conformational flexibility of the $C_\alpha$-atom using a homology model ensemble corresponding to the antibody, wherein the homology model ensemble comprises a three-dimensional model of an amino acid sequence of the antibody defined by one or more of the parameters listed in Table 2,
   c) determining for each Asp and Asn residue in the antibody Fv region the size of the amino acid residue directly C-terminal to the Asp or Asn residue,
   d) selecting one or more antibodies in which the $C_\alpha$-atom is conformationally inflexible and the Asp or Asn residue has a directly C-terminal naturally occurring amino acid residue with a solvent accessible surface area of 111 Å$^2$ or more,
   wherein conformational flexibility is the root mean square deviation (RMSD) of the Asn/Asp residues' $C_\alpha$-atoms in the homology model ensemble,
   and thereby selecting one or more antibodies with degradation stability of Asp and Asn residues.

2. The method according to claim 1, characterized in that the homology model ensemble is made with the antibody Fv region.

3. The method according to claim 1, characterized in that an amino acid residue with a solvent accessible surface area of less than 111 Å$^2$ is Gly, Ala, Ser, Cys, or Asp.

4. The method according to claim 3, characterized in that an amino acid residue with a solvent accessible surface area of less than 111 Å$^2$ is Gly, Ala, Ser, or Cys.

5. The method according to claim 1, wherein the antibody with degradation stability is produced according to the following steps:
   a) cultivating a mammalian cell comprising a nucleic acid encoding an antibody that has been selected with a method according to claim 1, and
   b) recovering the antibody from the cell or the cultivation medium and thereby producing the antibody.

6. The method according to claim 1, characterized in that
   i) conformational inflexible is a RMSD of 0.01 Å or less,
   ii) conformational flexible is a RMSD of more than 0.01 Å,
   iii) moderate conformational flexibility is a RMSD between 0.145 Å and 0.485 Å, and
   iv) high conformational flexibility is a RMSD of more than 0.485 Å.

* * * * *